(12) United States Patent
Terashima et al.

(10) Patent No.: US 8,034,630 B2
(45) Date of Patent: Oct. 11, 2011

(54) PROTEIN CAPABLE OF BINDING TO HYALURONIC ACID, AND METHOD FOR MEASUREMENT OF HYALURONIC ACID USING THE SAME

(75) Inventors: Kazuhiro Terashima, Amagasaki (JP); Kazunari Fujio, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 12/936,246

(22) PCT Filed: Apr. 14, 2009

(86) PCT No.: PCT/JP2009/057506
§ 371 (c)(1),
(2), (4) Date: Oct. 4, 2010

(87) PCT Pub. No.: WO2009/128448
PCT Pub. Date: Oct. 22, 2009

(65) Prior Publication Data
US 2011/0053220 A1  Mar. 3, 2011

(30) Foreign Application Priority Data
Apr. 15, 2008 (JP) .................. 2008-106190

(51) Int. Cl.
*G01N 33/543* (2006.01)
*C07K 1/00* (2006.01)
(52) U.S. Cl. ...................................... 436/518; 530/350

(58) Field of Classification Search .................. 530/350; 436/518
See application file for complete search history.

(56) References Cited

U.S. PATENT DOCUMENTS
2007/0259380 A1   11/2007   Sumida et al.

FOREIGN PATENT DOCUMENTS
| JP | 06-041952 | 6/1994 |
| JP | 2732718 | 12/1997 |
| JP | 3424504 | 5/2003 |
| WO | 2005/114186 | 12/2005 |

OTHER PUBLICATIONS

Fujio et al., Clinical Chemistry, Jun. 2007, 53(6), PP178, 59th Annual Meeting of the American Association of Cloinical Chemistry, San Diego, CA, USA.*
Hering, T.M. et al., "Complete Coding Sequence of Bovine Aggrecan: Comparative Structural Analysis," Archives of Biochemistry and Biophysics, vol. 345, No. 2, (1997) p. 259-270.
Watanabe, H. et al., "Identification of Hyaluronan-binding Domains of Aggrecan," Journal of Biological Chemistry, vol. 272, No. 44, (1997) p. 28057-28065.

* cited by examiner

*Primary Examiner* — Maryam Monshipouri
(74) *Attorney, Agent, or Firm* — Hamre, Schumann, Mueller & Larson, P.C.

(57) ABSTRACT

The present invention relates to a polynucleotide encoding a protein comprising an amino acid sequence shown in SEQ ID NO: 2, wherein the protein encoded by the polynucleotide has a hyaluronic acid binding ability, the protein, a method for measuring hyaluronic acid using the protein, and a reagent kit for measuring hyaluronic acid comprising the protein as a constituent.

5 Claims, 4 Drawing Sheets

[Fig.1]
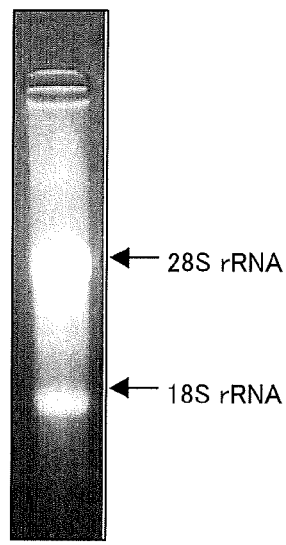
[Fig.2]
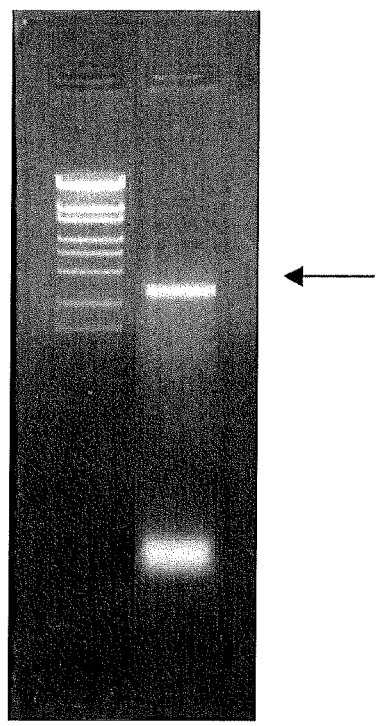

[Fig.3]
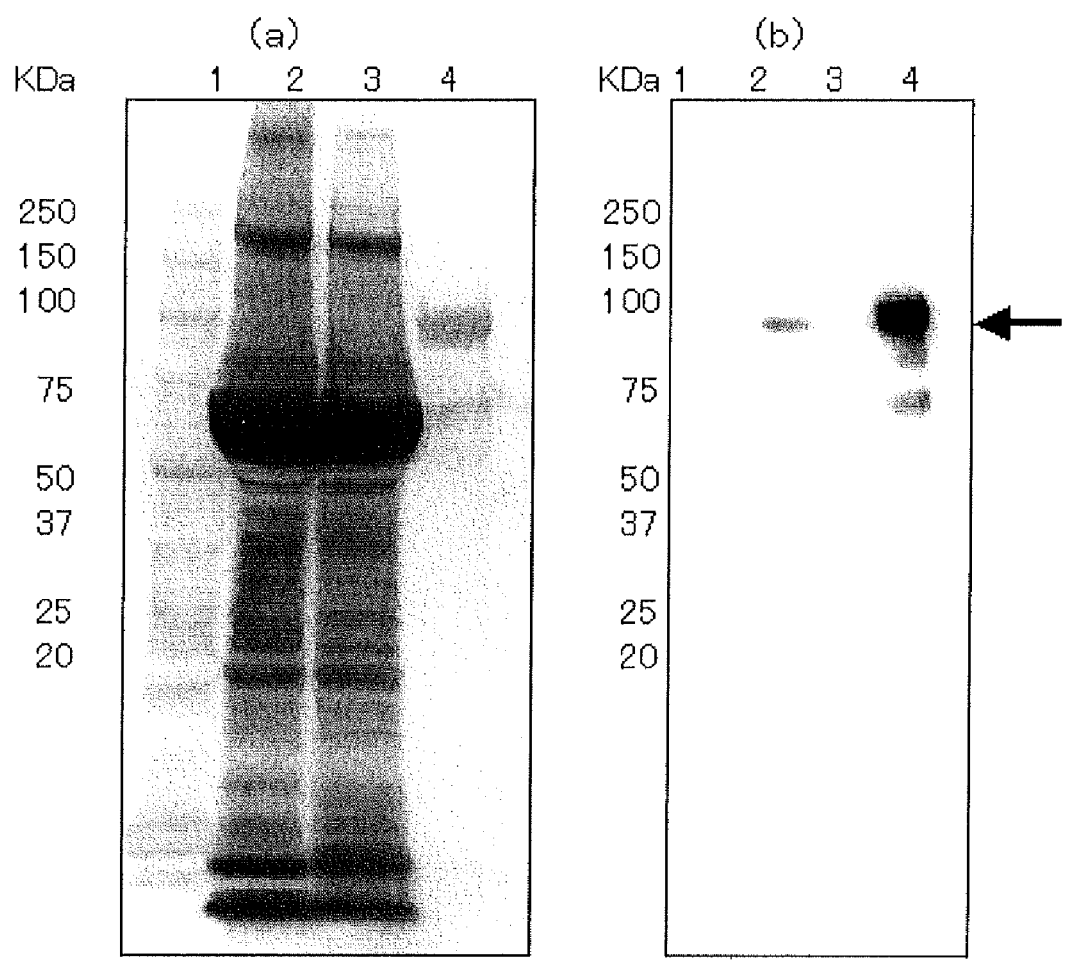

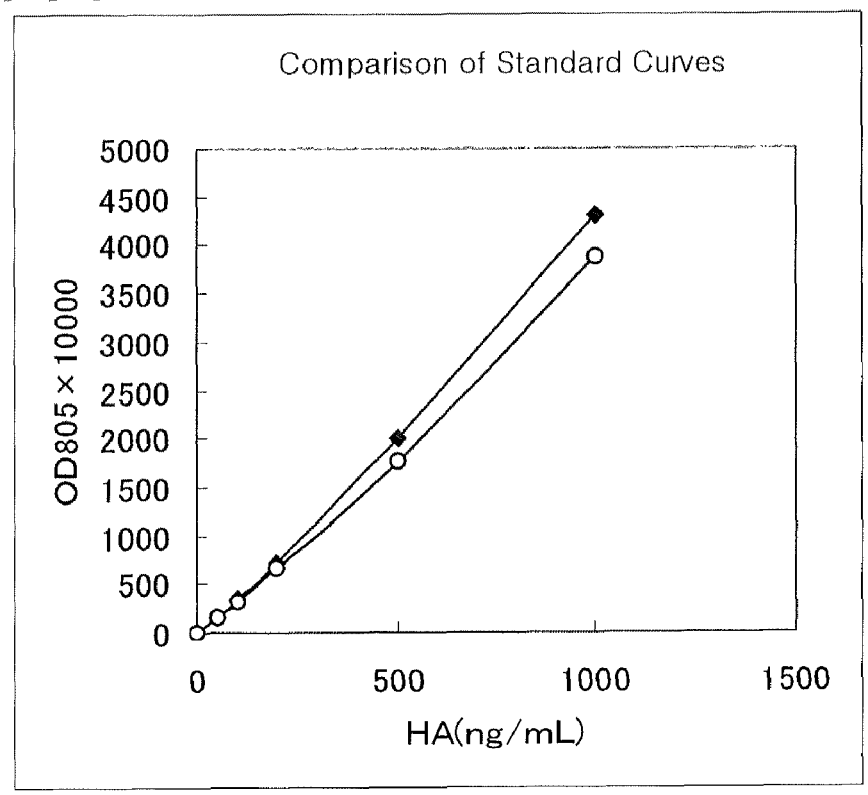
[Fig.4]

[Fig.5]
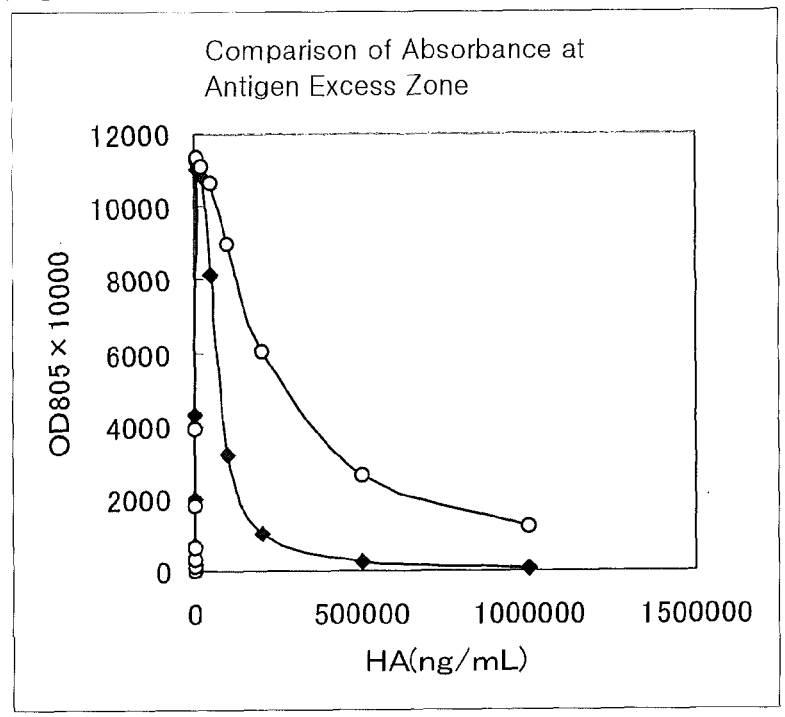
[Fig.6]
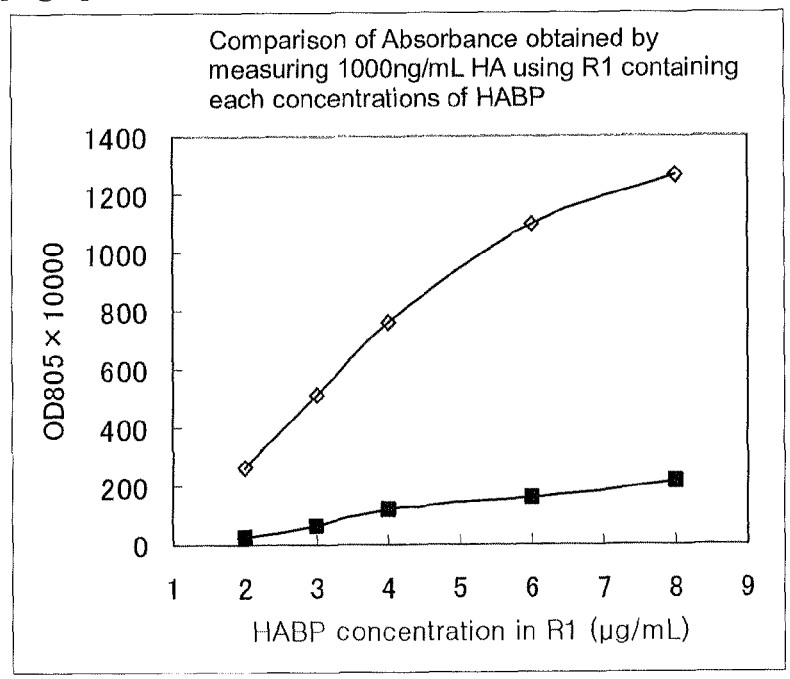

SEQUENCE LISTING

```
<160> NUMBER OF SEQ ID NOS: 9

<210> SEQ ID NO 1
<211> LENGTH: 2076
<212> TYPE: DNA
<213> ORGANISM: Bos taurus
<220> FEATURE:
<221> NAME/KEY: CDS
<222> LOCATION: (1)..(2076)
<220> FEATURE:
<221> NAME/KEY: misc_feature
<222> LOCATION: (393)..(393)
<223> OTHER INFORMATION: n is a, c, g, or t

<400> SEQUENCE: 1 atg acc act tta ctc ttg gtg ttt gtg act ctg agg gtc atc aca gca        48
Met Thr Thr Leu Leu Leu Val Phe Val Thr Leu Arg Val Ile Thr Ala
1               5                   10                  15 gcc atc tca gta gaa gtt tca gaa cct gac aac tcg ctg agt gtc agc        96
Ala Ile Ser Val Glu Val Ser Glu Pro Asp Asn Ser Leu Ser Val Ser
                20                  25                  30 atc cct gaa ccg tcc cca ctt cgg gtc ctc ctg ggg agc tcc ctc acc       144
Ile Pro Glu Pro Ser Pro Leu Arg Val Leu Leu Gly Ser Ser Leu Thr
            35                  40                  45 atc ccc tgc tac ttc atc gac ccc atg cac ccc gtg acc acc gcc ccc       192
Ile Pro Cys Tyr Phe Ile Asp Pro Met His Pro Val Thr Thr Ala Pro
        50                  55                  60 tcc acc gcc ccc ctt gcc cca aga atc aag tgg agc cgc att tcc aag       240
Ser Thr Ala Pro Leu Ala Pro Arg Ile Lys Trp Ser Arg Ile Ser Lys
65                  70                  75                  80 gag aag gag gtg gtg ctg ctg gtg gcc act gaa ggg cgg gtg cgg gtc       288
Glu Lys Glu Val Val Leu Leu Val Ala Thr Glu Gly Arg Val Arg Val
                85                  90                  95 aac agc gcc tac caa gac aag gtc acg ctg ccc aac tac ccc gcc atc       336
Asn Ser Ala Tyr Gln Asp Lys Val Thr Leu Pro Asn Tyr Pro Ala Ile
                100                 105                 110 ccc agc gac gcc acc ctg gaa atc cag aac atg cgc tcc aat gac tcc       384
Pro Ser Asp Ala Thr Leu Glu Ile Gln Asn Met Arg Ser Asn Asp Ser
            115                 120                 125 ggg ath hvn cgc tgc gag gtg atg cac ggc atc gag gac agc cag gcc       432
Gly Ile Xaa Arg Cys Glu Val Met His Gly Ile Glu Asp Ser Gln Ala
        130                 135                 140 acc cta gag gtc gtg gta aaa ggc atc gtg ttc cat tac aga gcc atc       480
Thr Leu Glu Val Val Val Lys Gly Ile Val Phe His Tyr Arg Ala Ile
145                 150                 155                 160 tcc acg cgc tac acc ctg gac ttt gac agg gcg cag cgg gcc tgc ctg       528
Ser Thr Arg Tyr Thr Leu Asp Phe Asp Arg Ala Gln Arg Ala Cys Leu
                165                 170                 175 cag aac agc gcc atc atc gcc acg ccc gag cag ctg cag gct gcc tat       576
Gln Asn Ser Ala Ile Ile Ala Thr Pro Glu Gln Leu Gln Ala Ala Tyr
                180                 185                 190 gag gac ggc ttc cac cag tgc gac gcc ggc tgg ctg gcc gat cag act       624
```

|   |   |   |
|---|---|---|
| Glu Asp Gly Phe His Gln Cys Asp Ala Gly Trp Leu Ala Asp Gln Thr<br>195 200 205 |   |   |
| gtg agg tat ccc atc cac acg ccg agg gaa ggt tgc tat gga gac aag<br>Val Arg Tyr Pro Ile His Thr Pro Arg Glu Gly Cys Tyr Gly Asp Lys<br>210 215 220 |   | 672 |
| gac gag ttt ccc ggc gtg aga acc tac ggc atc cgg gac acc aac gaa<br>Asp Glu Phe Pro Gly Val Arg Thr Tyr Gly Ile Arg Asp Thr Asn Glu<br>225 230 235 240 |   | 720 |
| acc tat gac gtg tac tgc ttc gcg gag gag atg gag ggc gag gtc ttc<br>Thr Tyr Asp Val Tyr Cys Phe Ala Glu Glu Met Glu Gly Glu Val Phe<br>245 250 255 |   | 768 |
| tat gca aca tcc ccg gag aag ttc acc ttc caa gag gca gcc aac gag<br>Tyr Ala Thr Ser Pro Glu Lys Phe Thr Phe Gln Glu Ala Ala Asn Glu<br>260 265 270 |   | 816 |
| tgc cgg cgg ctg ggc gcc cgg ctg gcc acc acg ggc caa ctc tac ctg<br>Cys Arg Arg Leu Gly Ala Arg Leu Ala Thr Thr Gly Gln Leu Tyr Leu<br>275 280 285 |   | 864 |
| gcc tgg cag ggt ggc atg gac atg tgc agc gcc ggc tgg ctg gct gac<br>Ala Trp Gln Gly Gly Met Asp Met Cys Ser Ala Gly Trp Leu Ala Asp<br>290 295 300 |   | 912 |
| cgc agc gtg cga tac ccc atc tcc aag gcc cgg cct aac tgc ggg ggc<br>Arg Ser Val Arg Tyr Pro Ile Ser Lys Ala Arg Pro Asn Cys Gly Gly<br>305 310 315 320 |   | 960 |
| aac ctc ctg gga gtg agg acc gtc tac ctg cac gcc aac cag acg ggc<br>Asn Leu Leu Gly Val Arg Thr Val Tyr Leu His Ala Asn Gln Thr Gly<br>325 330 335 |   | 1008 |
| tac cct gac cct tca tcc cgc tat gac gcc atc tgc tac aca ggt gaa<br>Tyr Pro Asp Pro Ser Ser Arg Tyr Asp Ala Ile Cys Tyr Thr Gly Glu<br>340 345 350 |   | 1056 |
| gac ttt gtg gac atc cca gaa agc ttt ttc ggg gtg ggc ggt gag gag<br>Asp Phe Val Asp Ile Pro Glu Ser Phe Phe Gly Val Gly Gly Glu Glu<br>355 360 365 |   | 1104 |
| gac atc acc atc cag acg gtg acc tgg cct gac gtg gag ctg ccc ctg<br>Asp Ile Thr Ile Gln Thr Val Thr Trp Pro Asp Val Glu Leu Pro Leu<br>370 375 380 |   | 1152 |
| ccc cga aat atc act gag ggt gaa gcc cga ggc agc gtg atc ctc acg<br>Pro Arg Asn Ile Thr Glu Gly Glu Ala Arg Gly Ser Val Ile Leu Thr<br>385 390 395 400 |   | 1200 |
| gca aag ccc gac ttt gaa gtc tcc ccc acc gcc ccg gaa ccc gag gag<br>Ala Lys Pro Asp Phe Glu Val Ser Pro Thr Ala Pro Glu Pro Glu Glu<br>405 410 415 |   | 1248 |
| cct ttc acg ttt gtc cct gaa gta agg gcc act gca ttc ccc gaa gta<br>Pro Phe Thr Phe Val Pro Glu Val Arg Ala Thr Ala Phe Pro Glu Val<br>420 425 430 |   | 1296 |
| gag aac agg act gaa gag gcc acc cgg ccc tgg gcc ttt ccc aga gag<br>Glu Asn Arg Thr Glu Glu Ala Thr Arg Pro Trp Ala Phe Pro Arg Glu<br>435 440 445 |   | 1344 |
| tcc acc ccc ggc ctg gga gcc ccc acg gcc ttc acc agc gag gac ctc<br>Ser Thr Pro Gly Leu Gly Ala Pro Thr Ala Phe Thr Ser Glu Asp Leu<br>450 455 460 |   | 1392 |
| gtc gtg cag gtg acc tta gcc cca ggt gcg gct gag gtc cct ggg cag<br>Val Val Gln Val Thr Leu Ala Pro Gly Ala Ala Glu Val Pro Gly Gln<br>465 470 475 480 |   | 1440 |
| cca cga ctg cca ggg gga gtc gtg ttc cac tac cgc ccg ggc tcc tcc<br>Pro Arg Leu Pro Gly Gly Val Val Phe His Tyr Arg Pro Gly Ser Ser<br>485 490 495 |   | 1488 |
| cgc tac tcg ctg acc ttt gag gag gcc aag cag gcc tgc ctg cgc acc<br>Arg Tyr Ser Leu Thr Phe Glu Glu Ala Lys Gln Ala Cys Leu Arg Thr<br>500 505 510 |   | 1536 |
| ggg gcc atc atc gcc tcg ccc gag cag ctc cag gcc gcc tat gaa gca<br>|   | 1584 |

```
        Gly Ala Ile Ile Ala Ser Pro Glu Gln Leu Gln Ala Ala Tyr Glu Ala
                515                 520                 525 ggc tac gag cag tgt gac gcc ggc tgg ctg cag gac cag aca gtc aga         1632
Gly Tyr Glu Gln Cys Asp Ala Gly Trp Leu Gln Asp Gln Thr Val Arg
        530                 535                 540 tac ccc att gtg agc ccg cgg acc ccc tgt gtg ggt gac aag gac agc         1680
Tyr Pro Ile Val Ser Pro Arg Thr Pro Cys Val Gly Asp Lys Asp Ser
545                 550                 555                 560 agc ccg ggg gtc cgg acc tac ggc gtg cgg cca cca tca gaa acc tac         1728
Ser Pro Gly Val Arg Thr Tyr Gly Val Arg Pro Pro Ser Glu Thr Tyr
                565                 570                 575 gat gtc tac tgc tac gtg gac aga ctc gag ggg gag gtg ttc ttc gcc         1776
Asp Val Tyr Cys Tyr Val Asp Arg Leu Glu Gly Glu Val Phe Phe Ala
        580                 585                 590 aca cgc ctg gag cag ttc acc ttc tgg gaa gcc cag gag ttc tgt gaa         1824
Thr Arg Leu Glu Gln Phe Thr Phe Trp Glu Ala Gln Glu Phe Cys Glu
                595                 600                 605 tcc caa aac gcc act ctg gcc acc aca ggc cag ctc tat gct gcc tgg         1872
Ser Gln Asn Ala Thr Leu Ala Thr Thr Gly Gln Leu Tyr Ala Ala Trp
        610                 615                 620 agc cgt ggt ctg gac aag tgc tac gcc ggc tgg ctg gct gac ggc agc         1920
Ser Arg Gly Leu Asp Lys Cys Tyr Ala Gly Trp Leu Ala Asp Gly Ser
625                 630                 635                 640 ctc cgc tac ccc atc gtc acc cca agg ccc gcc tgt ggc ggg gac aaa         1968
Leu Arg Tyr Pro Ile Val Thr Pro Arg Pro Ala Cys Gly Gly Asp Lys
                645                 650                 655 ccg ggc gtg aga acc gtc tac ctc tac ccc aac cag acg ggc ctc ctg         2016
Pro Gly Val Arg Thr Val Tyr Leu Tyr Pro Asn Gln Thr Gly Leu Leu
        660                 665                 670 gat ccg ctg tcc cgg cac cac gcc ttc tgc ttc cga ggt gtt tca gcg         2064
Asp Pro Leu Ser Arg His His Ala Phe Cys Phe Arg Gly Val Ser Ala
                675                 680                 685 gcg ccc tct cca                                                         2076
Ala Pro Ser Pro
        690

<210> SEQ ID NO 2
<211> LENGTH: 692
<212> TYPE: PRT
<213> ORGANISM: Bos taurus
<220> FEATURE:
<221> NAME/KEY: misc_feature
<222> LOCATION: (131)..(131)
<223> OTHER INFORMATION: The 'Xaa' at location 131 stands for Lys, Asn,
      Arg, Ser, Thr, Gln, His, Pro, Tyr, Trp, or Cys.

<400> SEQUENCE: 2

Met Thr Thr Leu Leu Leu Val Phe Val Thr Leu Arg Val Ile Thr Ala
1               5                   10                  15

Ala Ile Ser Val Glu Val Ser Glu Pro Asp Asn Ser Leu Ser Val Ser
                20                  25                  30

Ile Pro Glu Pro Ser Pro Leu Arg Val Leu Gly Ser Ser Leu Thr
        35                  40                  45

Ile Pro Cys Tyr Phe Ile Asp Pro Met His Pro Val Thr Thr Ala Pro
    50                  55                  60

Ser Thr Ala Pro Leu Ala Pro Arg Ile Lys Trp Ser Arg Ile Ser Lys
65              70                  75                  80

Glu Lys Glu Val Val Leu Leu Val Ala Thr Glu Gly Arg Val Arg Val
                85                  90                  95

Asn Ser Ala Tyr Gln Asp Lys Val Thr Leu Pro Asn Tyr Pro Ala Ile
            100                 105                 110
```

```
Pro Ser Asp Ala Thr Leu Glu Ile Gln Asn Met Arg Ser Asn Asp Ser
        115                 120                 125

Gly Ile Xaa Arg Cys Glu Val Met His Gly Ile Glu Asp Ser Gln Ala
    130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Gly Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Ser Phe Phe Gly Val Gly Gly Glu Glu
        355                 360                 365

Asp Ile Thr Ile Gln Thr Val Thr Trp Pro Asp Val Glu Leu Pro Leu
    370                 375                 380

Pro Arg Asn Ile Thr Glu Gly Glu Ala Arg Gly Ser Val Ile Leu Thr
385                 390                 395                 400

Ala Lys Pro Asp Phe Glu Val Ser Pro Thr Ala Pro Glu Pro Glu Glu
                405                 410                 415

Pro Phe Thr Phe Val Pro Glu Val Arg Ala Thr Ala Phe Pro Glu Val
            420                 425                 430

Glu Asn Arg Thr Glu Glu Ala Thr Arg Pro Trp Ala Phe Pro Arg Glu
        435                 440                 445

Ser Thr Pro Gly Leu Gly Ala Pro Thr Ala Phe Thr Ser Glu Asp Leu
    450                 455                 460

Val Val Gln Val Thr Leu Ala Pro Gly Ala Ala Glu Val Pro Gly Gln
465                 470                 475                 480

Pro Arg Leu Pro Gly Gly Val Phe His Tyr Arg Pro Gly Ser Ser
                485                 490                 495

Arg Tyr Ser Leu Thr Phe Glu Glu Ala Lys Gln Ala Cys Leu Arg Thr
            500                 505                 510

Gly Ala Ile Ile Ala Ser Pro Glu Gln Leu Gln Ala Ala Tyr Glu Ala
        515                 520                 525

Gly Tyr Glu Gln Cys Asp Ala Gly Trp Leu Gln Asp Gln Thr Val Arg
```

```
                530              535              540
Tyr Pro Ile Val Ser Pro Arg Thr Pro Cys Val Gly Asp Lys Asp Ser
545                  550                  555                  560

Ser Pro Gly Val Arg Thr Tyr Gly Val Arg Pro Pro Ser Glu Thr Tyr
                 565                  570                  575

Asp Val Tyr Cys Tyr Val Asp Arg Leu Glu Gly Glu Val Phe Phe Ala
                 580                  585                  590

Thr Arg Leu Glu Gln Phe Thr Phe Trp Glu Ala Gln Glu Phe Cys Glu
                 595                  600                  605

Ser Gln Asn Ala Thr Leu Ala Thr Thr Gly Gln Leu Tyr Ala Ala Trp
                 610                  615                  620

Ser Arg Gly Leu Asp Lys Cys Tyr Ala Gly Trp Leu Ala Asp Gly Ser
625                  630                  635                  640

Leu Arg Tyr Pro Ile Val Thr Pro Arg Pro Ala Cys Gly Gly Asp Lys
                 645                  650                  655

Pro Gly Val Arg Thr Val Tyr Leu Tyr Pro Asn Gln Thr Gly Leu Leu
                 660                  665                  670

Asp Pro Leu Ser Arg His His Ala Phe Cys Phe Arg Gly Val Ser Ala
                 675                  680                  685

Ala Pro Ser Pro
690

<210> SEQ ID NO 3
<211> LENGTH: 2076
<212> TYPE: DNA
<213> ORGANISM: Bos taurus
<220> FEATURE:
<221> NAME/KEY: CDS
<222> LOCATION: (1)..(2076)

<400> SEQUENCE: 3 atg acc act tta ctc ttg gtg ttt gtg act ctg agg gtc atc aca gca      48
Met Thr Thr Leu Leu Leu Val Phe Val Thr Leu Arg Val Ile Thr Ala
1               5                   10                  15 gcc atc tca gta gaa gtt tca gaa cct gac aac tcg ctg agt gtc agc      96
Ala Ile Ser Val Glu Val Ser Glu Pro Asp Asn Ser Leu Ser Val Ser
                20                  25                  30 atc cct gaa ccg tcc cca ctt cgg gtc ctc ctg ggg agc tcc ctc acc     144
Ile Pro Glu Pro Ser Pro Leu Arg Val Leu Leu Gly Ser Ser Leu Thr
            35                  40                  45 atc ccc tgc tac ttc atc gac ccc atg cac ccc gtg acc acc gcc ccc     192
Ile Pro Cys Tyr Phe Ile Asp Pro Met His Pro Val Thr Thr Ala Pro
        50                  55                  60 tcc acc gcc ccc ctt gcc cca aga atc aag tgg agc cgc att tcc aag     240
Ser Thr Ala Pro Leu Ala Pro Arg Ile Lys Trp Ser Arg Ile Ser Lys
65                  70                  75                  80 gag aag gag gtg gtg ctg ctg gtg gcc act gaa ggg cgg gtg cgg gtc     288
Glu Lys Glu Val Val Leu Leu Val Ala Thr Glu Gly Arg Val Arg Val
                85                  90                  95 aac agc gcc tac caa gac aag gtc acg ctg ccc aac tac ccc gcc atc     336
Asn Ser Ala Tyr Gln Asp Lys Val Thr Leu Pro Asn Tyr Pro Ala Ile
                100                 105                 110 ccc agc gac gcc acc ctg gaa atc cag aac atg cgc tcc aat gac tcc     384
Pro Ser Asp Ala Thr Leu Glu Ile Gln Asn Met Arg Ser Asn Asp Ser
            115                 120                 125 ggg atc tat cgc tgc gag gtg atg cac ggc atc gag gac agc cag gcc     432
Gly Ile Tyr Arg Cys Glu Val Met His Gly Ile Glu Asp Ser Gln Ala
        130                 135                 140 acc cta gag gtc gtg gta aaa ggc atc gtg ttc cat tac aga gcc atc     480
```

```
        Thr Leu Glu Val Val Lys Gly Ile Val Phe His Tyr Arg Ala Ile
        145                 150                 155                 160 tcc acg cgc tac acc ctg gac ttt gac agg gcg cag cgg gcc tgc ctg      528
Ser Thr Arg Tyr Thr Leu Asp Phe Asp Arg Ala Gln Arg Ala Cys Leu
            165                 170                 175 cag aac agc gcc atc atc gcc acg ccc gag cag ctg cag gct gcc tat      576
Gln Asn Ser Ala Ile Ile Ala Thr Pro Glu Gln Leu Gln Ala Ala Tyr
        180                 185                 190 gag gac ggc ttc cac cag tgc gac gcc ggc tgg ctg gcc gat cag act      624
Glu Asp Gly Phe His Gln Cys Asp Ala Gly Trp Leu Ala Asp Gln Thr
            195                 200                 205 gtg agg tat ccc atc cac acg ccg agg gaa ggt tgc tat gga gac aag      672
Val Arg Tyr Pro Ile His Thr Pro Arg Glu Gly Cys Tyr Gly Asp Lys
    210                 215                 220 gac gag ttt ccc ggc gtg aga acc tac ggc atc cgg gac acc aac gaa      720
Asp Glu Phe Pro Gly Val Arg Thr Tyr Gly Ile Arg Asp Thr Asn Glu
225                 230                 235                 240 acc tat gac gtg tac tgc ttc gcg gag gag atg gag ggc gag gtc ttc      768
Thr Tyr Asp Val Tyr Cys Phe Ala Glu Glu Met Glu Gly Glu Val Phe
                245                 250                 255 tat gca aca tcc ccg gag aag ttc acc ttc caa gag gca gcc aac gag      816
Tyr Ala Thr Ser Pro Glu Lys Phe Thr Phe Gln Glu Ala Ala Asn Glu
            260                 265                 270 tgc cgg cgg ctg ggc gcc cgg ctg gcc acc acg ggc caa ctc tac ctg      864
Cys Arg Arg Leu Gly Ala Arg Leu Ala Thr Thr Gly Gln Leu Tyr Leu
        275                 280                 285 gcc tgg cag ggt ggc atg gac atg tgc agc gcc ggc tgg ctg gct gac      912
Ala Trp Gln Gly Gly Met Asp Met Cys Ser Ala Gly Trp Leu Ala Asp
    290                 295                 300 cgc agc gtg cga tac ccc atc tcc aag gcc cgg cct aac tgc ggg ggc      960
Arg Ser Val Arg Tyr Pro Ile Ser Lys Ala Arg Pro Asn Cys Gly Gly
305                 310                 315                 320 aac ctc ctg gga gtg agg acc gtc tac ctg cac gcc aac cag acg ggc     1008
Asn Leu Leu Gly Val Arg Thr Val Tyr Leu His Ala Asn Gln Thr Gly
                325                 330                 335 tac cct gac cct tca tcc cgc tat gac gcc atc tgc tac aca ggt gaa     1056
Tyr Pro Asp Pro Ser Ser Arg Tyr Asp Ala Ile Cys Tyr Thr Gly Glu
            340                 345                 350 gac ttt gtg gac atc cca gaa agc ttt ttc ggg gtg ggc ggt gag gag     1104
Asp Phe Val Asp Ile Pro Glu Ser Phe Phe Gly Val Gly Gly Glu Glu
        355                 360                 365 gac atc acc atc cag acg gtg acc tgg cct gac gtg gag ctg ccc ctg     1152
Asp Ile Thr Ile Gln Thr Val Thr Trp Pro Asp Val Glu Leu Pro Leu
    370                 375                 380 ccc cga aat atc act gag ggt gaa gcc cga ggc agc gtg atc ctc acg     1200
Pro Arg Asn Ile Thr Glu Gly Glu Ala Arg Gly Ser Val Ile Leu Thr
385                 390                 395                 400 gca aag ccc gac ttt gaa gtc tcc ccc acc gcc ccg gaa ccc gag gag     1248
Ala Lys Pro Asp Phe Glu Val Ser Pro Thr Ala Pro Glu Pro Glu Glu
                405                 410                 415 cct ttc acg ttt gtc cct gaa gta agg gcc act gca ttc ccc gaa gta     1296
Pro Phe Thr Phe Val Pro Glu Val Arg Ala Thr Ala Phe Pro Glu Val
            420                 425                 430 gag aac agg act gaa gag gcc acc cgg ccc tgg gcc ttt ccc aga gag     1344
Glu Asn Arg Thr Glu Glu Ala Thr Arg Pro Trp Ala Phe Pro Arg Glu
        435                 440                 445 tcc acc ccc ggc ctg gga gcc ccc acg gcc ttc acc agc gag gac ctc     1392
Ser Thr Pro Gly Leu Gly Ala Pro Thr Ala Phe Thr Ser Glu Asp Leu
    450                 455                 460 gtc gtg cag gtg acc tta gcc cca ggt gcg gct gag gtc cct ggg cag     1440
```

```
Val Val Gln Val Thr Leu Ala Pro Gly Ala Ala Glu Val Pro Gly Gln
465                 470                 475                 480 cca cga ctg cca ggg gga gtc gtg ttc cac tac cgc ccg ggc tcc tcc    1488
Pro Arg Leu Pro Gly Gly Val Val Phe His Tyr Arg Pro Gly Ser Ser
                    485                 490                 495 cgc tac tcg ctg acc ttt gag gag gcc aag cag gcc tgc ctg cgc acc    1536
Arg Tyr Ser Leu Thr Phe Glu Glu Ala Lys Gln Ala Cys Leu Arg Thr
                500                 505                 510 ggg gcc atc atc gcc tcg ccc gag cag ctc cag gcc gcc tat gaa gca    1584
Gly Ala Ile Ile Ala Ser Pro Glu Gln Leu Gln Ala Ala Tyr Glu Ala
            515                 520                 525 ggc tac gag cag tgt gac gcc ggc tgg ctg cag gac cag aca gtc aga    1632
Gly Tyr Glu Gln Cys Asp Ala Gly Trp Leu Gln Asp Gln Thr Val Arg
        530                 535                 540 tac ccc att gtg agc ccg cgg acc ccc tgt gtg ggt gac aag gac agc    1680
Tyr Pro Ile Val Ser Pro Arg Thr Pro Cys Val Gly Asp Lys Asp Ser
545                 550                 555                 560 agc ccg ggg gtc cgg acc tac ggc gtg cgg cca cca tca gaa acc tac    1728
Ser Pro Gly Val Arg Thr Tyr Gly Val Arg Pro Pro Ser Glu Thr Tyr
                565                 570                 575 gat gtc tac tgc tac gtg gac aga ctc gag ggg gag gtg ttc ttc gcc    1776
Asp Val Tyr Cys Tyr Val Asp Arg Leu Glu Gly Glu Val Phe Phe Ala
                580                 585                 590 aca cgc ctg gag cag ttc acc ttc tgg gaa gcc cag gag ttc tgt gaa    1824
Thr Arg Leu Glu Gln Phe Thr Phe Trp Glu Ala Gln Glu Phe Cys Glu
            595                 600                 605 tcc caa aac gcc act ctg gcc acc aca ggc cag ctc tat gct gcc tgg    1872
Ser Gln Asn Ala Thr Leu Ala Thr Thr Gly Gln Leu Tyr Ala Ala Trp
        610                 615                 620 agc cgt ggt ctg gac aag tgc tac gcc ggc tgg ctg gct gac ggc agc    1920
Ser Arg Gly Leu Asp Lys Cys Tyr Ala Gly Trp Leu Ala Asp Gly Ser
625                 630                 635                 640 ctc cgc tac ccc atc gtc acc cca agg ccc gcc tgt ggc ggg gac aaa    1968
Leu Arg Tyr Pro Ile Val Thr Pro Arg Pro Ala Cys Gly Gly Asp Lys
                645                 650                 655 ccg ggc gtg aga acc gtc tac ctc tac ccc aac cag acg ggc ctc ctg    2016
Pro Gly Val Arg Thr Val Tyr Leu Tyr Pro Asn Gln Thr Gly Leu Leu
                660                 665                 670 gat ccg ctg tcc cgg cac cac gcc ttc tgc ttc cga ggt gtt tca gcg    2064
Asp Pro Leu Ser Arg His His Ala Phe Cys Phe Arg Gly Val Ser Ala
            675                 680                 685 gcg ccc tct cca                                                    2076
Ala Pro Ser Pro
        690

<210> SEQ ID NO 4
<211> LENGTH: 692
<212> TYPE: PRT
<213> ORGANISM: Bos taurus

<400> SEQUENCE: 4

Met Thr Thr Leu Leu Leu Val Phe Val Thr Leu Arg Val Ile Thr Ala
1               5                   10                  15

Ala Ile Ser Val Glu Val Ser Glu Pro Asp Asn Ser Leu Ser Val Ser
                20                  25                  30

Ile Pro Glu Pro Ser Pro Leu Arg Val Leu Leu Gly Ser Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Ile Ser Lys
```

```
                65                  70                  75                  80
            Glu Lys Glu Val Val Leu Leu Val Ala Thr Glu Gly Arg Val Arg Val
                                85                  90                  95
            Asn Ser Ala Tyr Gln Asp Lys Val Thr Leu Pro Asn Tyr Pro Ala Ile
                               100                 105                 110
            Pro Ser Asp Ala Thr Leu Glu Ile Gln Asn Met Arg Ser Asn Asp Ser
                               115                 120                 125
            Gly Ile Tyr Arg Cys Glu Val Met His Gly Ile Glu Asp Ser Gln Ala
                               130                 135                 140
            Thr Leu Glu Val Val Lys Gly Ile Val Phe His Tyr Arg Ala Ile
            145                 150                 155                 160
            Ser Thr Arg Tyr Thr Leu Asp Phe Asp Arg Ala Gln Arg Ala Cys Leu
                               165                 170                 175
            Gln Asn Ser Ala Ile Ile Ala Thr Pro Glu Gln Leu Gln Ala Ala Tyr
                               180                 185                 190
            Glu Asp Gly Phe His Gln Cys Asp Ala Gly Trp Leu Ala Asp Gln Thr
                               195                 200                 205
            Val Arg Tyr Pro Ile His Thr Pro Arg Glu Gly Cys Tyr Gly Asp Lys
            210                 215                 220
            Asp Glu Phe Pro Gly Val Arg Thr Tyr Gly Ile Arg Asp Thr Asn Glu
            225                 230                 235                 240
            Thr Tyr Asp Val Tyr Cys Phe Ala Glu Glu Met Glu Gly Glu Val Phe
                               245                 250                 255
            Tyr Ala Thr Ser Pro Glu Lys Phe Thr Phe Gln Glu Ala Ala Asn Glu
                               260                 265                 270
            Cys Arg Arg Leu Gly Ala Arg Leu Ala Thr Thr Gly Gln Leu Tyr Leu
                               275                 280                 285
            Ala Trp Gln Gly Gly Met Asp Met Cys Ser Ala Gly Trp Leu Ala Asp
                               290                 295                 300
            Arg Ser Val Arg Tyr Pro Ile Ser Lys Ala Arg Pro Asn Cys Gly Gly
            305                 310                 315                 320
            Asn Leu Leu Gly Val Arg Thr Val Tyr Leu His Ala Asn Gln Thr Gly
                               325                 330                 335
            Tyr Pro Asp Pro Ser Ser Arg Tyr Asp Ala Ile Cys Tyr Thr Gly Glu
                               340                 345                 350
            Asp Phe Val Asp Ile Pro Glu Ser Phe Gly Val Gly Gly Glu Glu
                               355                 360                 365
            Asp Ile Thr Ile Gln Thr Val Thr Trp Pro Asp Val Glu Leu Pro Leu
                               370                 375                 380
            Pro Arg Asn Ile Thr Glu Gly Glu Ala Arg Gly Ser Val Ile Leu Thr
            385                 390                 395                 400
            Ala Lys Pro Asp Phe Glu Val Ser Pro Thr Ala Pro Glu Pro Glu Glu
                               405                 410                 415
            Pro Phe Thr Phe Val Pro Glu Val Arg Ala Thr Ala Phe Pro Glu Val
                               420                 425                 430
            Glu Asn Arg Thr Glu Glu Ala Thr Arg Pro Trp Ala Phe Pro Arg Glu
                               435                 440                 445
            Ser Thr Pro Gly Leu Gly Ala Pro Thr Ala Phe Thr Ser Glu Asp Leu
                               450                 455                 460
            Val Val Gln Val Thr Leu Ala Pro Gly Ala Ala Glu Val Pro Gly Gln
            465                 470                 475                 480
            Pro Arg Leu Pro Gly Gly Val Val Phe His Tyr Arg Pro Gly Ser Ser
                               485                 490                 495
```

```
Arg Tyr Ser Leu Thr Phe Glu Glu Ala Lys Gln Ala Cys Leu Arg Thr
            500                 505                 510

Gly Ala Ile Ile Ala Ser Pro Glu Gln Leu Gln Ala Ala Tyr Glu Ala
        515                 520                 525

Gly Tyr Glu Gln Cys Asp Ala Gly Trp Leu Gln Asp Gln Thr Val Arg
    530                 535                 540

Tyr Pro Ile Val Ser Pro Arg Thr Pro Cys Val Gly Asp Lys Asp Ser
545                 550                 555                 560

Ser Pro Gly Val Arg Thr Tyr Gly Val Arg Pro Ser Glu Thr Tyr
                565                 570                 575

Asp Val Tyr Cys Tyr Val Asp Arg Leu Glu Gly Glu Val Phe Phe Ala
                580                 585                 590

Thr Arg Leu Glu Gln Phe Thr Phe Trp Glu Ala Gln Glu Phe Cys Glu
            595                 600                 605

Ser Gln Asn Ala Thr Leu Ala Thr Thr Gly Gln Leu Tyr Ala Ala Trp
        610                 615                 620

Ser Arg Gly Leu Asp Lys Cys Tyr Ala Gly Trp Leu Ala Asp Gly Ser
625                 630                 635                 640

Leu Arg Tyr Pro Ile Val Thr Pro Arg Pro Ala Cys Gly Gly Asp Lys
                645                 650                 655

Pro Gly Val Arg Thr Val Tyr Leu Tyr Pro Asn Gln Thr Gly Leu Leu
            660                 665                 670

Asp Pro Leu Ser Arg His His Ala Phe Cys Phe Arg Gly Val Ser Ala
        675                 680                 685

Ala Pro Ser Pro
    690

<210> SEQ ID NO 5
<211> LENGTH: 33
<212> TYPE: DNA
<213> ORGANISM: Artificial
<220> FEATURE:
<223> OTHER INFORMATION: oligonucleotide primer

<400> SEQUENCE: 5
atgaattcat gaccacttta ctcttggtgt ttg                                33

<210> SEQ ID NO 6
<211> LENGTH: 35
<212> TYPE: DNA
<213> ORGANISM: Artificial
<220> FEATURE:
<223> OTHER INFORMATION: oligonucleotide primer

<400> SEQUENCE: 6
atgaattctc atggagaggg cgccgctgaa acacc                              35

<210> SEQ ID NO 7
<211> LENGTH: 2327
<212> TYPE: PRT
<213> ORGANISM: Bos taurus

<400> SEQUENCE: 7

Met Thr Thr Leu Leu Leu Val Phe Val Thr Leu Arg Val Ile Thr Ala
1               5                   10                  15

Ala Ile Ser Val Glu Val Ser Glu Pro Asp Asn Ser Leu Ser Val Ser
            20                  25                  30

Ile Pro Glu Pro Ser Pro Leu Arg Val Leu Leu Gly Ser Ser Leu Thr
        35                  40                  45
```

```
Ile Pro Cys Tyr Phe Ile Asp Pro Met His Pro Val Thr Ala Pro
    50                  55                  60

Ser Thr Ala Pro Leu Ala Pro Arg Ile Lys Trp Ser Arg Ile Ser Lys
 65              70                  75                      80

Glu Lys Glu Val Val Leu Leu Val Ala Thr Glu Gly Arg Val Arg Val
                85                  90                  95

Asn Ser Ala Tyr Gln Asp Lys Val Thr Leu Pro Asn Tyr Pro Ala Ile
            100                 105                 110

Pro Ser Asp Ala Thr Leu Glu Ile Gln Asn Met Arg Ser Asn Asp Ser
        115                 120                 125

Gly Ile Leu Arg Cys Glu Val Met His Gly Ile Glu Asp Ser Gln Ala
    130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Gly Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Ser Phe Phe Gly Val Gly Gly Glu Glu
        355                 360                 365

Asp Ile Thr Ile Gln Thr Val Thr Trp Pro Asp Val Glu Leu Pro Leu
    370                 375                 380

Pro Arg Asn Ile Thr Glu Gly Glu Ala Arg Gly Ser Val Ile Leu Thr
385                 390                 395                 400

Ala Lys Pro Asp Phe Glu Val Ser Pro Thr Ala Pro Glu Pro Glu Glu
                405                 410                 415

Pro Phe Thr Phe Val Pro Glu Val Arg Ala Thr Ala Phe Pro Glu Val
            420                 425                 430

Glu Asn Arg Thr Glu Glu Ala Thr Arg Pro Trp Ala Phe Pro Arg Glu
        435                 440                 445

Ser Thr Pro Gly Leu Gly Ala Pro Thr Ala Phe Thr Ser Glu Asp Leu
    450                 455                 460

Val Val Gln Val Thr Leu Ala Pro Gly Ala Ala Glu Val Pro Gly Gln
465                 470                 475                 480
```

-continued

Pro Arg Leu Pro Gly Gly Val Val Phe His Tyr Arg Pro Gly Ser Ser
                485                 490                 495

Arg Tyr Ser Leu Thr Phe Glu Glu Ala Lys Gln Ala Cys Leu Arg Thr
            500                 505                 510

Gly Ala Ile Ile Ala Ser Pro Glu Gln Leu Gln Ala Ala Tyr Glu Ala
            515                 520                 525

Gly Tyr Glu Gln Cys Asp Ala Gly Trp Leu Gln Asp Gln Thr Val Arg
        530                 535                 540

Tyr Pro Ile Val Ser Pro Arg Thr Pro Cys Val Gly Asp Lys Asp Ser
545                 550                 555                 560

Ser Pro Gly Val Arg Thr Tyr Gly Val Arg Pro Ser Glu Thr Tyr
                565                 570                 575

Asp Val Tyr Cys Tyr Val Asp Arg Leu Glu Gly Glu Val Phe Phe Ala
                580                 585                 590

Thr Arg Leu Glu Gln Phe Thr Phe Trp Glu Ala Gln Glu Phe Cys Glu
        595                 600                 605

Ser Gln Asn Ala Thr Leu Ala Thr Thr Gly Gln Leu Tyr Ala Ala Trp
        610                 615                 620

Ser Arg Gly Leu Asp Lys Cys Tyr Ala Gly Trp Leu Ala Asp Gly Ser
625                 630                 635                 640

Leu Arg Tyr Pro Ile Val Thr Pro Arg Pro Ala Cys Gly Gly Asp Lys
                645                 650                 655

Pro Gly Val Arg Thr Val Tyr Leu Tyr Pro Asn Gln Thr Gly Leu Leu
                660                 665                 670

Asp Pro Leu Ser Arg His His Ala Phe Cys Phe Arg Gly Val Ser Ala
        675                 680                 685

Ala Pro Ser Pro Glu Glu Glu Gly Ser Ala Pro Thr Ala Gly Pro
        690                 695                 700

Asp Val Glu Glu Trp Met Val Thr Gln Val Gly Pro Gly Val Ala Ala
705                 710                 715                 720

Val Pro Ile Gly Glu Glu Thr Thr Ala Ile Pro Gly Phe Thr Val Glu
                725                 730                 735

Pro Glu Asn Lys Thr Glu Trp Glu Leu Ala Tyr Thr Pro Ala Gly Thr
                740                 745                 750

Leu Pro Leu Pro Gly Ile Pro Pro Thr Trp Pro Pro Thr Gly Glu Ala
            755                 760                 765

Thr Glu Glu His Thr Glu Gly Pro Ser Ala Thr Glu Val Pro Ser Ala
        770                 775                 780

Ser Glu Lys Pro Phe Pro Ser Glu Glu Pro Phe Pro Glu Glu Pro
785                 790                 795                 800

Phe Pro Ser Glu Lys Pro Phe Pro Glu Glu Leu Phe Pro Ser Glu
                805                 810                 815

Lys Pro Phe Pro Ser Glu Lys Pro Phe Pro Ser Glu Glu Pro Phe Pro
            820                 825                 830

Ser Glu Lys Pro Phe Pro Glu Glu Leu Phe Pro Ser Glu Lys Pro
        835                 840                 845

Ile Pro Ser Glu Glu Pro Phe Pro Ser Glu Glu Pro Phe Pro Ser Glu
        850                 855                 860

Lys Pro Phe Pro Glu Glu Pro Phe Pro Ser Glu Lys Pro Ile Pro
865                 870                 875                 880

Ser Glu Glu Pro Phe Pro Ser Glu Lys Pro Phe Pro Ser Glu Glu Pro
                885                 890                 895

Phe Pro Ser Glu Glu Pro Ser Thr Leu Ser Ala Pro Val Pro Ser Arg

```
                    900                 905                 910
Thr Glu Leu Pro Ser Ser Gly Glu Val Ser Gly Val Pro Glu Ile Ser
        915                 920                 925

Gly Asp Phe Thr Gly Ser Gly Glu Ile Ser Gly His Leu Asp Phe Ser
        930                 935                 940

Gly Gln Pro Ser Gly Glu Ser Ala Ser Gly Leu Pro Ser Glu Asp Leu
945                 950                 955                 960

Asp Ser Ser Gly Leu Thr Ser Thr Val Gly Ser Gly Leu Pro Val Glu
                965                 970                 975

Ser Gly Leu Pro Ser Gly Glu Glu Arg Ile Thr Trp Thr Ser Ala
        980                 985                 990

Pro Lys Val Asp Arg Leu Pro Ser  Gly Gly Glu Gly  Pro Glu Val Ser
        995                 1000                1005

Gly Val  Glu Asp Ile Ser Gly  Leu Pro Ser Gly  Gly Glu Val His
    1010                1015                1020

Leu Glu  Ile Ser Ala Ser Gly  Val Glu Asp Ile Ser  Gly Leu Pro
    1025                1030                1035

Ser Gly  Gly Glu Val His Leu  Glu Ile Ser Ala Ser  Gly Val Glu
    1040                1045                1050

Asp Leu  Ser Arg Ile Pro Ser  Gly Glu Gly Pro Glu  Ile Ser Ala
    1055                1060                1065

Ser Gly  Val Glu Asp Ile Ser  Gly Leu Pro Ser Gly  Glu Glu Gly
    1070                1075                1080

His Leu  Glu Ile Ser Ala Ser  Gly Val Glu Asp Leu  Ser Gly Ile
    1085                1090                1095

Pro Ser  Gly Glu Gly Pro Glu  Val Ser Ala Ser Gly  Val Glu Asp
    1100                1105                1110

Leu Ile  Gly Leu Pro Ser Gly  Glu Gly Pro Glu Val  Ser Ala Ser
    1115                1120                1125

Gly Val  Glu Asp Leu Ser Arg  Leu Pro Ser Gly Glu  Gly Pro Glu
    1130                1135                1140

Val Ser  Ala Ser Gly Val Glu  Asp Leu Ser Gly Leu  Pro Ser Gly
    1145                1150                1155

Glu Gly  Pro Glu Val Ser Val  Ser Gly Val Glu Asp  Leu Ser Arg
    1160                1165                1170

Leu Pro  Ser Gly Glu Gly Pro  Glu Val Ser Ala Ser  Gly Val Glu
    1175                1180                1185

Asp Leu  Ser Arg Leu Pro Ser  Gly Glu Gly Pro Glu  Ile Ser Val
    1190                1195                1200

Ser Gly  Val Glu Asp Ile Ser  Ile Leu Pro Ser Gly  Glu Gly Pro
    1205                1210                1215

Glu Val  Ser Ala Ser Gly Val  Glu Asp Leu Ser Val  Leu Pro Ser
    1220                1225                1230

Gly Glu  Gly His Leu Glu Ile  Ser Thr Ser Gly Val  Glu Asp Leu
    1235                1240                1245

Ser Val  Leu Pro Ser Gly Glu  Gly His Leu Glu Thr  Ser Ser Gly
    1250                1255                1260

Val Glu  Asp Ile Ser Arg Leu  Pro Ser Gly Glu Gly  Pro Glu Val
    1265                1270                1275

Ser Ala  Ser Gly Val Glu Asp  Leu Ser Val Leu Pro  Ser Gly Glu
    1280                1285                1290

Asp His  Leu Glu Ile Ser Ala  Ser Gly Val Glu Asp  Leu Gly Val
    1295                1300                1305
```

-continued

```
Leu Pro Ser Gly Glu Asp His Leu Glu Ile Ser Ala Ser Gly Val
    1310                1315                1320
Glu Asp Ile Ser Arg Leu Pro Ser Gly Glu Gly Pro Glu Val Ser
    1325                1330                1335
Ala Ser Gly Val Glu Asp Leu Ser Val Leu Pro Ser Gly Glu Gly
    1340                1345                1350
His Leu Glu Ile Ser Ala Ser Gly Val Glu Asp Leu Ser Arg Leu
    1355                1360                1365
Pro Ser Gly Gly Glu Asp His Leu Glu Thr Ser Ala Ser Gly Val
    1370                1375                1380
Gly Asp Leu Ser Gly Leu Pro Ser Gly Arg Glu Gly Leu Glu Ile
    1385                1390                1395
Ser Ala Ser Gly Ala Gly Asp Leu Ser Gly Leu Thr Ser Gly Lys
    1400                1405                1410
Glu Asp Leu Thr Gly Ser Ala Ser Gly Ala Leu Asp Leu Gly Arg
    1415                1420                1425
Ile Pro Ser Val Thr Leu Gly Ser Gly Gln Ala Pro Glu Ala Ser
    1430                1435                1440
Gly Leu Pro Ser Gly Phe Ser Gly Glu Tyr Ser Gly Val Asp Leu
    1445                1450                1455
Glu Ser Gly Pro Ser Ser Gly Leu Pro Asp Phe Ser Gly Leu Pro
    1460                1465                1470
Ser Gly Phe Pro Thr Val Ser Leu Val Asp Thr Thr Leu Val Glu
    1475                1480                1485
Val Val Thr Ala Thr Thr Ala Gly Glu Leu Glu Gly Arg Gly Thr
    1490                1495                1500
Ile Asp Ile Ser Gly Ala Gly Glu Thr Ser Gly Leu Pro Phe Ser
    1505                1510                1515
Glu Leu Asp Ile Ser Gly Ala Ser Gly Leu Ser Ser Gly Ala
    1520                1525                1530
Glu Leu Ser Gly Gln Ala Ser Gly Ser Pro Asp Ile Ser Gly Glu
    1535                1540                1545
Thr Ser Gly Leu Phe Gly Val Ser Gly Gln Pro Ser Gly Phe Pro
    1550                1555                1560
Asp Ile Ser Gly Glu Thr Ser Gly Leu Leu Glu Val Ser Gly Gln
    1565                1570                1575
Pro Ser Gly Phe Tyr Gly Glu Ile Ser Gly Val Thr Glu Leu Ser
    1580                1585                1590
Gly Leu Ala Ser Gly Gln Pro Glu Ile Ser Gly Glu Ala Ser Gly
    1595                1600                1605
Ile Leu Ser Gly Leu Gly Pro Pro Phe Gly Ile Thr Asp Leu Ser
    1610                1615                1620
Gly Glu Ala Pro Gly Ile Pro Asp Leu Ser Gly Gln Pro Ser Gly
    1625                1630                1635
Leu Pro Glu Phe Ser Gly Thr Ala Ser Gly Ile Pro Asp Leu Val
    1640                1645                1650
Ser Ser Ala Val Ser Gly Ser Gly Glu Ser Ser Gly Ile Thr Phe
    1655                1660                1665
Val Asp Thr Ser Leu Val Glu Val Thr Pro Thr Thr Phe Lys Glu
    1670                1675                1680
Glu Glu Gly Leu Gly Ser Val Glu Leu Ser Gly Leu Pro Ser Gly
    1685                1690                1695
Glu Leu Gly Val Ser Gly Thr Ser Gly Leu Ala Asp Val Ser Gly
    1700                1705                1710
```

-continued

```
Leu Ser Ser Gly Ala Ile Asp Ser Ser Gly Phe Thr Ser Gln Pro
    1715                1720                1725

Pro Glu Phe Ser Gly Leu Pro Ser Gly Val Thr Glu Val Ser Gly
    1730                1735                1740

Glu Ala Ser Gly Ala Glu Ser Gly Ser Ser Leu Pro Ser Gly Ala
    1745                1750                1755

Tyr Asp Ser Ser Gly Leu Pro Ser Gly Phe Pro Thr Val Ser Phe
    1760                1765                1770

Val Asp Arg Thr Leu Val Glu Ser Val Thr Gln Ala Pro Thr Ala
    1775                1780                1785

Gln Glu Ala Gly Glu Gly Pro Ser Gly Ile Leu Glu Leu Ser Gly
    1790                1795                1800

Ala Pro Ser Gly Ala Pro Asp Met Ser Gly Asp His Leu Gly Ser
    1805                1810                1815

Leu Asp Gln Ser Gly Leu Gln Ser Gly Leu Val Glu Pro Ser Gly
    1820                1825                1830

Glu Pro Ala Ser Thr Pro Tyr Phe Ser Gly Asp Phe Ser Gly Thr
    1835                1840                1845

Thr Asp Val Ser Gly Glu Ser Ser Ala Ala Thr Ser Thr Ser Gly
    1850                1855                1860

Glu Ala Ser Gly Leu Pro Glu Val Thr Leu Ile Thr Ser Glu Leu
    1865                1870                1875

Val Glu Gly Val Thr Glu Pro Thr Val Ser Gln Glu Leu Gly Gln
    1880                1885                1890

Arg Pro Pro Val Thr Tyr Thr Pro Gln Leu Phe Glu Ser Ser Gly
    1895                1900                1905

Glu Ala Ser Ala Ser Gly Asp Val Pro Arg Phe Pro Gly Ser Gly
    1910                1915                1920

Val Glu Val Ser Ser Val Pro Glu Ser Ser Gly Glu Thr Ser Ala
    1925                1930                1935

Tyr Pro Glu Ala Glu Val Gly Ala Ser Ala Ala Pro Glu Ala Ser
    1940                1945                1950

Gly Gly Ala Ser Gly Ser Pro Asn Leu Ser Glu Thr Thr Ser Thr
    1955                1960                1965

Phe His Glu Ala Asp Leu Glu Gly Thr Ser Gly Leu Gly Val Ser
    1970                1975                1980

Gly Ser Pro Ser Ala Phe Pro Glu Gly Pro Thr Glu Gly Leu Ala
    1985                1990                1995

Thr Pro Glu Val Ser Gly Glu Ser Thr Thr Ala Phe Asp Val Ser
    2000                2005                2010

Val Glu Ala Ser Gly Ser Pro Ser Ala Thr Pro Leu Ala Ser Gly
    2015                2020                2025

Asp Arg Thr Asp Thr Ser Gly Asp Leu Ser Gly His Thr Ser Gly
    2030                2035                2040

Leu Asp Ile Val Ile Ser Thr Thr Ile Pro Glu Ser Glu Trp Thr
    2045                2050                2055

Gln Gln Thr Gln Arg Pro Ala Glu Ala Arg Leu Glu Ile Glu Ser
    2060                2065                2070

Ser Ser Pro Val His Ser Gly Glu Glu Ser Gln Thr Ala Asp Thr
    2075                2080                2085

Ala Thr Ser Pro Thr Asp Ala Ser Ile Pro Ala Ser Ala Gly Gly
    2090                2095                2100

Thr Asp Asp Ser Glu Ala Thr Thr Thr Asp Gln Lys Leu Cys Glu
```

-continued

```
                        2105                2110                2115
Glu Gly Trp Thr Lys Phe Gln Gly His Cys Tyr Arg His Phe Pro
    2120                2125                2130

Asp Arg Ala Thr Trp Val Asp Ala Glu Ser Gln Cys Arg Lys Gln
    2135                2140                2145

Gln Ser His Leu Ser Ser Ile Val Thr Pro Glu Glu Gln Glu Phe
    2150                2155                2160

Val Asn Asn Asn Ala Gln Asp Tyr Gln Trp Ile Gly Leu Asn Asp
    2165                2170                2175

Lys Thr Ile Glu Gly Asp Phe Arg Trp Ser Asp Gly His Ser Leu
    2180                2185                2190

Gln Phe Glu Asn Trp Arg Pro Asn Gln Pro Asp Asn Phe Phe Ala
    2195                2200                2205

Thr Gly Glu Asp Cys Val Val Met Ile Trp His Glu Lys Gly Glu
    2210                2215                2220

Trp Asn Asp Val Pro Cys Asn Tyr Gln Leu Pro Phe Thr Cys Lys
    2225                2230                2235

Lys Gly Thr Val Ala Cys Gly Glu Pro Pro Val Val Glu His Ala
    2240                2245                2250

Arg Ile Phe Gly Gln Lys Lys Asp Arg Tyr Glu Ile Asn Ala Leu
    2255                2260                2265

Val Arg Tyr Gln Cys Thr Glu Gly Phe Ile Gln Gly His Val Pro
    2270                2275                2280

Thr Ile Arg Cys Gln Pro Ser Gly His Trp Glu Glu Pro Arg Ile
    2285                2290                2295

Thr Cys Thr Asp Pro Ala Thr Tyr Lys Arg Arg Leu Gln Lys Arg
    2300                2305                2310

Ser Ser Arg Pro Leu Arg Arg Ser His Pro Ser Thr Ala His
    2315                2320                2325

<210> SEQ ID NO 8
<211> LENGTH: 2076
<212> TYPE: DNA
<213> ORGANISM: Bos taurus
<220> FEATURE:
<221> NAME/KEY: CDS
<222> LOCATION: (1)..(2076)

<400> SEQUENCE: 8 atg acc act tta ctc ttg gtg ttt gtg act ctg agg gtc atc aca gca    48
Met Thr Thr Leu Leu Leu Val Phe Val Thr Leu Arg Val Ile Thr Ala
1               5                   10                  15 gcc atc tca gta gaa gtt tca gaa cct gac aac tcg ctg agt gtc agc    96
Ala Ile Ser Val Glu Val Ser Glu Pro Asp Asn Ser Leu Ser Val Ser
                20                  25                  30 atc cct gaa ccg tcc cca ctt cgg gtc ctc ctg ggg agc tcc ctc acc   144
Ile Pro Glu Pro Ser Pro Leu Arg Val Leu Leu Gly Ser Ser Leu Thr
            35                  40                  45 atc ccc tgc tac ttc atc gac ccc atg cac ccc gtg acc acc gcc ccc   192
Ile Pro Cys Tyr Phe Ile Asp Pro Met His Pro Val Thr Thr Ala Pro
        50                  55                  60 tcc acc gcc ccc ctt gcc cca aga atc aag tgg agc cgc att tcc aag   240
Ser Thr Ala Pro Leu Ala Pro Arg Ile Lys Trp Ser Arg Ile Ser Lys
65                  70                  75                  80 gag aag gag gtg gtg ctg ctg gtg gcc act gaa ggg cgg gtg cgg gtc   288
Glu Lys Glu Val Val Leu Leu Val Ala Thr Glu Gly Arg Val Arg Val
                85                  90                  95 aac agc gcc tac caa gac aag gtc acg ctg ccc aac tac ccc gcc atc   336
```

```
                -continued

Asn Ser Ala Tyr Gln Asp Lys Val Thr Leu Pro Asn Tyr Pro Ala Ile
            100                 105                 110 ccc agc gac gcc acc ctg gaa atc cag aac atg cgc tcc aat gac tcc      384
Pro Ser Asp Ala Thr Leu Glu Ile Gln Asn Met Arg Ser Asn Asp Ser
            115                 120                 125 ggg att cta cgc tgc gag gtg atg cac ggc atc gag gac agc cag gcc      432
Gly Ile Leu Arg Cys Glu Val Met His Gly Ile Glu Asp Ser Gln Ala
        130                 135                 140 acc cta gag gtc gtg gta aaa ggc atc gtg ttc cat tac aga gcc atc      480
Thr Leu Glu Val Val Val Lys Gly Ile Val Phe His Tyr Arg Ala Ile
145                 150                 155                 160 tcc acg cgc tac acc ctg gac ttt gac agg gcg cag cgg gcc tgc ctg      528
Ser Thr Arg Tyr Thr Leu Asp Phe Asp Arg Ala Gln Arg Ala Cys Leu
                165                 170                 175 cag aac agc gcc atc atc gcc acg ccc gag cag ctg cag gct gcc tat      576
Gln Asn Ser Ala Ile Ile Ala Thr Pro Glu Gln Leu Gln Ala Ala Tyr
            180                 185                 190 gag gac ggc ttc cac cag tgc gac gcc ggc tgg ctg gcc gat cag act      624
Glu Asp Gly Phe His Gln Cys Asp Ala Gly Trp Leu Ala Asp Gln Thr
        195                 200                 205 gtg agg tat ccc atc cac acg ccg agg gaa ggt tgc tat gga gac aag      672
Val Arg Tyr Pro Ile His Thr Pro Arg Glu Gly Cys Tyr Gly Asp Lys
    210                 215                 220 gac gag ttt ccc ggc gtg aga acc tac ggc atc cgg gac acc aac gaa      720
Asp Glu Phe Pro Gly Val Arg Thr Tyr Gly Ile Arg Asp Thr Asn Glu
225                 230                 235                 240 acc tat gac gtg tac tgc ttc gcg gag gag atg gag ggc gag gtc ttc      768
Thr Tyr Asp Val Tyr Cys Phe Ala Glu Glu Met Glu Gly Glu Val Phe
                245                 250                 255 tat gca aca tcc ccg gag aag ttc acc ttc caa gag gca gcc aac gag      816
Tyr Ala Thr Ser Pro Glu Lys Phe Thr Phe Gln Glu Ala Ala Asn Glu
            260                 265                 270 tgc cgg cgg ctg ggc gcc cgg ctg gcc acc acg ggc caa ctc tac ctg      864
Cys Arg Arg Leu Gly Ala Arg Leu Ala Thr Thr Gly Gln Leu Tyr Leu
        275                 280                 285 gcc tgg cag ggt ggc atg gac atg tgc agc gcc ggc tgg ctg gct gac      912
Ala Trp Gln Gly Gly Met Asp Met Cys Ser Ala Gly Trp Leu Ala Asp
    290                 295                 300 cgc agc gtg cga tac ccc atc tcc aag gcc cgg cct aac tgc ggg ggc      960
Arg Ser Val Arg Tyr Pro Ile Ser Lys Ala Arg Pro Asn Cys Gly Gly
305                 310                 315                 320 aac ctc ctg gga gtg agg acc gtc tac ctg cac gcc aac cag acg ggc     1008
Asn Leu Leu Gly Val Arg Thr Val Tyr Leu His Ala Asn Gln Thr Gly
                325                 330                 335 tac cct gac cct tca tcc cgc tat gac gcc atc tgc tac aca ggt gaa     1056
Tyr Pro Asp Pro Ser Ser Arg Tyr Asp Ala Ile Cys Tyr Thr Gly Glu
            340                 345                 350 gac ttt gtg gac atc cca gaa agc ttt ttc ggg gtg ggc ggt gag gag     1104
Asp Phe Val Asp Ile Pro Glu Ser Phe Phe Gly Val Gly Gly Glu Glu
        355                 360                 365 gac atc acc atc cag acg gtg acc tgg cct gac gtg gag ctg ccc ctg     1152
Asp Ile Thr Ile Gln Thr Val Thr Trp Pro Asp Val Glu Leu Pro Leu
    370                 375                 380 ccc cga aat atc act gag ggt gaa gcc cga ggc agc gtg atc ctc acg     1200
Pro Arg Asn Ile Thr Glu Gly Glu Ala Arg Gly Ser Val Ile Leu Thr
385                 390                 395                 400 gca aag ccc gac ttt gaa gtc tcc ccc acc gcc ccg gaa ccc gag gag     1248
Ala Lys Pro Asp Phe Glu Val Ser Pro Thr Ala Pro Glu Pro Glu Glu
                405                 410                 415 cct ttc acg ttt gtc cct gaa gta agg gcc act gca ttc ccc gaa gta     1296
```

```
                Pro Phe Thr Phe Val Pro Glu Val Arg Ala Thr Ala Phe Pro Glu Val
                                420                 425                 430 gag aac agg act gaa gag gcc acc cgg ccc tgg gcc ttt ccc aga gag        1344
Glu Asn Arg Thr Glu Glu Ala Thr Arg Pro Trp Ala Phe Pro Arg Glu
                435                 440                 445 tcc acc ccc ggc ctg gga gcc ccc acg gcc ttc acc agc gag gac ctc        1392
Ser Thr Pro Gly Leu Gly Ala Pro Thr Ala Phe Thr Ser Glu Asp Leu
        450                 455                 460 gtc gtg cag gtg acc tta gcc cca ggt gcg gct gag gtc cct ggg cag        1440
Val Val Gln Val Thr Leu Ala Pro Gly Ala Ala Glu Val Pro Gly Gln
465                 470                 475                 480 cca cga ctg cca ggg gga gtc gtg ttc cac tac cgc ccg ggc tcc tcc        1488
Pro Arg Leu Pro Gly Gly Val Val Phe His Tyr Arg Pro Gly Ser Ser
                485                 490                 495 cgc tac tcg ctg acc ttt gag gag gcc aag cag gcc tgc ctg cgc acc        1536
Arg Tyr Ser Leu Thr Phe Glu Glu Ala Lys Gln Ala Cys Leu Arg Thr
                500                 505                 510 ggg gcc atc atc gcc tcg ccc gag cag ctc cag gcc gcc tat gaa gca        1584
Gly Ala Ile Ile Ala Ser Pro Glu Gln Leu Gln Ala Ala Tyr Glu Ala
        515                 520                 525 ggc tac gag cag tgt gac gcc ggc tgg ctg cag gac cag aca gtc aga        1632
Gly Tyr Glu Gln Cys Asp Ala Gly Trp Leu Gln Asp Gln Thr Val Arg
    530                 535                 540 tac ccc att gtg agc ccg cgg acc ccc tgt gtg ggt gac aag gac agc        1680
Tyr Pro Ile Val Ser Pro Arg Thr Pro Cys Val Gly Asp Lys Asp Ser
545                 550                 555                 560 agc ccg ggg gtc cgg acc tac ggc gtg cgg cca cca tca gaa acc tac        1728
Ser Pro Gly Val Arg Thr Tyr Gly Val Arg Pro Pro Ser Glu Thr Tyr
                565                 570                 575 gat gtc tac tgc tac gtg gac aga ctc gag ggg gag gtg ttc ttc gcc        1776
Asp Val Tyr Cys Tyr Val Asp Arg Leu Glu Gly Glu Val Phe Phe Ala
                580                 585                 590 aca cgc ctg gag cag ttc acc ttc tgg gaa gcc cag gag ttc tgt gaa        1824
Thr Arg Leu Glu Gln Phe Thr Phe Trp Glu Ala Gln Glu Phe Cys Glu
        595                 600                 605 tcc caa aac gcc act ctg gcc acc aca ggc cag ctc tat gct gcc tgg        1872
Ser Gln Asn Ala Thr Leu Ala Thr Thr Gly Gln Leu Tyr Ala Ala Trp
    610                 615                 620 agc cgt ggt ctg gac aag tgc tac gcc ggc tgg ctg gct gac ggc agc        1920
Ser Arg Gly Leu Asp Lys Cys Tyr Ala Gly Trp Leu Ala Asp Gly Ser
625                 630                 635                 640 ctc cgc tac ccc atc gtc acc cca agg ccc gcc tgt ggc ggg gac aaa        1968
Leu Arg Tyr Pro Ile Val Thr Pro Arg Pro Ala Cys Gly Gly Asp Lys
                645                 650                 655 ccg ggc gtg aga acc gtc tac ctc tac ccc aac cag acg ggc ctc ctg        2016
Pro Gly Val Arg Thr Val Tyr Leu Tyr Pro Asn Gln Thr Gly Leu Leu
                660                 665                 670 gat ccg ctg tcc cgg cac cac gcc ttc tgc ttc cga ggt gtt tca gcg        2064
Asp Pro Leu Ser Arg His His Ala Phe Cys Phe Arg Gly Val Ser Ala
        675                 680                 685 gcg ccc tct cca                                                        2076
Ala Pro Ser Pro
    690

<210> SEQ ID NO 9
<211> LENGTH: 692
<212> TYPE: PRT
<213> ORGANISM: Bos taurus

<400> SEQUENCE: 9

Met Thr Thr Leu Leu Leu Val Phe Val Thr Leu Arg Val Ile Thr Ala
```

-continued

```
1               5                   10                  15
Ala Ile Ser Val Glu Val Ser Glu Pro Asp Asn Ser Leu Ser Val Ser
                20                  25                  30

Ile Pro Glu Pro Ser Pro Leu Arg Val Leu Leu Gly Ser Ser Leu Thr
                35                  40              45

Ile Pro Cys Tyr Phe Ile Asp Pro Met His Pro Val Thr Thr Ala Pro
            50                  55                  60

Ser Thr Ala Pro Leu Ala Pro Arg Ile Lys Trp Ser Arg Ile Ser Lys
65                  70                  75                  80

Glu Lys Glu Val Val Leu Leu Val Ala Thr Glu Gly Arg Val Arg Val
                    85                  90                  95

Asn Ser Ala Tyr Gln Asp Lys Val Thr Leu Pro Asn Tyr Pro Ala Ile
                100                 105                 110

Pro Ser Asp Ala Thr Leu Glu Ile Gln Asn Met Arg Ser Asn Asp Ser
                115                 120                 125

Gly Ile Leu Arg Cys Glu Val Met His Gly Ile Glu Asp Ser Gln Ala
            130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
                180                 185                 190

Glu Asp Gly Phe His Gln Cys Asp Ala Gly Trp Leu Ala Asp Gln Thr
                195                 200                 205

Val Arg Tyr Pro Ile His Thr Pro Arg Glu Gly Cys Tyr Gly Asp Lys
210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
                260                 265                 270

Cys Arg Arg Leu Gly Ala Arg Leu Ala Thr Thr Gly Gln Leu Tyr Leu
                275                 280                 285

Ala Trp Gln Gly Gly Met Asp Met Cys Ser Ala Gly Trp Leu Ala Asp
            290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
                340                 345                 350

Asp Phe Val Asp Ile Pro Glu Ser Phe Phe Gly Val Gly Gly Glu Glu
                355                 360                 365

Asp Ile Thr Ile Gln Thr Val Thr Trp Pro Asp Val Glu Leu Pro Leu
370                 375                 380

Pro Arg Asn Ile Thr Glu Gly Glu Ala Arg Gly Ser Val Ile Leu Thr
385                 390                 395                 400

Ala Lys Pro Asp Phe Glu Val Ser Pro Thr Ala Pro Glu Pro Glu Glu
                405                 410                 415

Pro Phe Thr Phe Val Pro Glu Val Arg Ala Thr Ala Phe Pro Glu Val
                420                 425                 430
```

```
Glu Asn Arg Thr Glu Glu Ala Thr Arg Pro Trp Ala Phe Pro Arg Glu
            435                 440                 445

Ser Thr Pro Gly Leu Gly Ala Pro Thr Ala Phe Thr Ser Glu Asp Leu
    450                 455                 460

Val Val Gln Val Thr Leu Ala Pro Gly Ala Ala Glu Val Pro Gly Gln
465                 470                 475                 480

Pro Arg Leu Pro Gly Gly Val Val Phe His Tyr Arg Pro Gly Ser Ser
            485                 490                 495

Arg Tyr Ser Leu Thr Phe Glu Glu Ala Lys Gln Ala Cys Leu Arg Thr
            500                 505                 510

Gly Ala Ile Ile Ala Ser Pro Glu Gln Leu Gln Ala Ala Tyr Glu Ala
            515                 520                 525

Gly Tyr Glu Gln Cys Asp Ala Gly Trp Leu Gln Asp Gln Thr Val Arg
            530                 535                 540

Tyr Pro Ile Val Ser Pro Arg Thr Pro Cys Val Gly Asp Lys Asp Ser
545                 550                 555                 560

Ser Pro Gly Val Arg Thr Tyr Gly Val Arg Pro Pro Ser Glu Thr Tyr
                565                 570                 575

Asp Val Tyr Cys Tyr Val Asp Arg Leu Glu Gly Glu Val Phe Phe Ala
            580                 585                 590

Thr Arg Leu Glu Gln Phe Thr Phe Trp Glu Ala Gln Glu Phe Cys Glu
            595                 600                 605

Ser Gln Asn Ala Thr Leu Ala Thr Thr Gly Gln Leu Tyr Ala Ala Trp
    610                 615                 620

Ser Arg Gly Leu Asp Lys Cys Tyr Ala Gly Trp Leu Ala Asp Gly Ser
625                 630                 635                 640

Leu Arg Tyr Pro Ile Val Thr Pro Arg Pro Ala Cys Gly Gly Asp Lys
            645                 650                 655

Pro Gly Val Arg Thr Val Tyr Leu Tyr Pro Asn Gln Thr Gly Leu Leu
            660                 665                 670

Asp Pro Leu Ser Arg His His Ala Phe Cys Phe Arg Gly Val Ser Ala
            675                 680                 685

Ala Pro Ser Pro
    690
```

US 8,034,630 B2

PROTEIN CAPABLE OF BINDING TO HYALURONIC ACID, AND METHOD FOR MEASUREMENT OF HYALURONIC ACID USING THE SAME

This application is a 371 of PCT/JP2009/057506, filed Apr. 14, 2009, which claims foreign priority to Japanese Application No. 2008-106190, filed Apr. 15, 2008.

TECHNICAL FIELD

The present invention relates to a novel protein having a hyaluronic acid binding ability (a hyaluronic acid binding protein, hereinafter, sometimes abbreviated as HABP) which is inexpensive and superior in stability of quality, a method for measuring hyaluronic acid with high degree of accuracy in measurement, and a reagent kit using the same.

BACKGROUND ART

Hyaluronic acid is a kind of mucopolysaccharide, and contained mainly in the synovial fluid and ocular vitreous humor of animal, and in connective tissues such as the umbilical cord and the upper dermis, and the like, of animals. It has been known that concentration thereof in blood rises when affected by rheumatoid disease, cancer or hepatic disease, and hence, hyaluronic acid is thought to be useful for diagnosis of these diseases, and various measuring methods have been developed to date.

As a method for measuring hyaluronic acid, a method in which measurement is performed by the enzyme-linked immunosorbent assay (ELISA) using HABP (Patent Literature: 1, Patent Literature: 2, and the like) or an immunological measurement method using latex particles are known.

Among them, the immunological measurement method using latex particles has been widely employed, because of its simple procedure and applicability to multipurpose measuring devices. As a measurement method using latex particles as a reagent for measuring hyaluronic acid, a method comprising processes of supporting HABP on carrier particles, reacting HABP with hyaluronic acid in the sample to form a reaction complex, and determining the hyaluronic acid by detecting the reaction complex (Patent Literature: 3), and the like are known.

On the other hand, as HABP, proteoglycans such as aggrecan, and the like, link protein and hyaluronectin, and the like are known. Among them, aggrecan is a proteoglycan of high molecular-weight, which accounts for about 90% of proteoglycan present in cartilage, contains chondroitin sulfate, and is present in cartilage tissue in a form binding to hyaluronic acid. In addition, aggrecan is also used for measurement of hyaluronic acid.

However, since aggrecan that has been heretofore used for measurement of hyaluronic acid is a purified product from bovine cartilage, aggrecan has problems such that it has a fluctuation in quality from lot to lot due to native product and expensive price thereof.

Therefore, a development of HABP which has no fluctuation in quality and is inexpensive and a method for obtaining the HABP has been desired.

CITATION LIST

Patent Literature

Patent Literature 1: JP-B-Hei 20273041 6 041952
Patent Literature 2: JP-B-2732718
Patent Literature 3: JP-B-3424504

SUMMARY OF INVENTION

Technical Problem

On the view of the above situation, an object of the present invention is to provide a novel HABP, a method for obtaining HABP having no fluctuation in quality as well as at an inexpensive price, a method for measuring hyaluronic acid with high degree of accuracy in measurement, and a reagent kit using the same.

Solution to Problem

The present invention was made for the purpose of solving the above described problems, and have found that cDNA comprising a nucleotide sequence encoding an amino acid sequence having high homology to the known amino acid sequence of bovine aggrecan, which the aggrecan is a kind of HABP, can be obtained from a cDNA library prepared from the bovine cartilage mRNA. In addition, the present inventors have found that the HABP of the present invention can be obtained by transfecting the host cell with a recombinant expression vector comprising the cDNA, and culturing the host cell to express the cDNA.

In addition, the present inventors have found that by carrying out the measurement of hyaluronic acid using the HABP of the present invention, a high-accuracy measurement of hyaluronic acid can be done without fluctuation in quality, and with a prozone phenomenon being inhibited, in comparison with the measurement method for hyaluronic acid using conventional native aggrecan.

Namely, the present invention comprises the following compositions:

(1) A polynucleotide encoding a protein having a hyaluronic acid binding ability comprising an amino acid sequence shown in SEQ ID NO: 2, wherein the amino acid sequence has an isoleucine residue in position 130 from N-terminal of the amino acid sequence, and a residue derived from an amino acid selected from the group consisting of tyrosine, serine, threonine, cysteine, asparagine and glutamine in position 131 from N-terminal of the amino acid sequence.

(2) A protein having a hyaluronic acid binding ability, wherein the protein comprises an amino acid sequence shown in SEQ ID NO: 2; an amino acid residue in position 130 from N-terminal of the amino acid sequence is isoleucine; an amino acid residue in position 131 is a residue derived from an amino acid selected from the group consisting of tyrosine, serine, threonine, cysteine, asparagine and glutamine.

(3) A method for producing the protein having a hyaluronic acid binding ability described in the above (2), comprising;

culturing a host cell transfected by Baculovirus integrated with a recombinant expression vector having a polynucleotide comprising the nucleotide sequence shown in SEQ ID NO:1, or a transformant obtained by transforming the host cells by the recombinant expression vector, and separating and purifying a protein from the culture medium.

(4) A method for measuring hyaluronic acid, comprising;

contacting a hyaluronic acid in a sample with the protein having a hyaluronic acid binding ability described in above (2) to form a complex of the hyaluronic acid and the protein, reacting the complex with a carrier supporting an antibody specific to the protein, measuring an optical change by an agglutinate obtained from the reaction, and calculating an amount of the hyaluronic acid from the measured value.

(5) A reagent kit for measuring a hyaluronic acid, comprising the protein having a hyaluronic acid binding ability described in the above (2) as a constituent.

Advantageous Effects of Invention

The present invention provides a novel and inexpensive HABP having no fluctuation among products. Since the HABP of the present invention is a recombinant product, the HABP can be obtained at an inexpensive cost and in a large amount, and has superior quality with no fluctuation in quality, in comparison with native aggrecan.

In addition, since the HABP of the present invention has features described above, inexpensive and high-accuracy measurement of hyaluronic acid can be performed using this.

BRIEF DESCRIPTION OF DRAWINGS

FIG. 1 shows the results of electrophoresis of the total RNA solution recovered from bovine cartilage of nasal septum on 1% agarose gel, which was obtained in the Example 1 (1). In addition, the arrows in FIG. 1 show fractions of 18s rRNA and 28s rRNA, respectively.

FIG. 2 shows the results of electrophoresis of the PCR product on agarose gel containing ethidium bromide, which is obtained in Example 1 (3). In FIG. 2, lane 1 shows the result when molecular weight marker was used as a sample, and lane 2 shows the result when fragment of PCR product was used as a sample, respectively. In addition, the arrow shows a fraction of the fragment of PCR product.

FIG. 3 shows the results obtained in Example 1 (7). In FIG. 3, (a) shows the result of the silver staining of the gel after SDS-PAGE, and (b) shows the result of Western blotting using peroxidase-labeled anti-Aggrecan antibody. In addition, in FIGS. 3 (a) and (b), each lane shows the results when the following sample was used: lane 1: the molecular weight marker of protein, lane 2: the culture supernatant before affinity purification, lane 3: the culture supernatant after affinity purification, and lane 4: the protein obtained by affinity purification. Further, the arrow in FIG. 3 (b) shows a fraction of the HABP of the present invention.

FIG. 4 shows the standard curves showing relationships between concentrations of hyaluronic acid in the samples and absorbances of the sample at 805 nm, which were obtained in Example 2 and Comparative Example 1.

FIG. 5 shows the results of plotting the absorbance at 805 nm of the samples for concentrations of hyaluronic acid, which were obtained in Example 3 and the Comparative Example 2.

FIG. 6 shows the result of plotting the absorbance at 805 nm of samples containing 1,000 ng/mL of hyaluronic acid for each HABP concentration in the first reagent in the cases when various concentrations of the HABP of the present invention or the HABP of the known amino acid sequence were used, which were obtained in Example 4 and Comparative Example 3.

DESCRIPTION OF EMBODIMENTS

Aggrecan derived from bovine cartilage (*Bos taurus* aggrecan) is a protein having a hyaluronic acid binding ability, i.e. HAPB, having of 2,327 amino acids in total. In addition, mapping of the gene sequence thereof has already been completed, and the sequence and the entire amino acid sequence have been disclosed in DNA Data Bank of Japan (DDBJ). The known entire amino acid sequence derived from bovine aggrecan disclosed in the above mentioned database is shown in SEQ ID NO: 7. Hyaluronic acid binding site of the bovine aggrecan is located in a part of amino acid residues in positions 153 to 352 from N-terminal of the sequence.

The polynucleotide of the present invention is similar to "a polynucleotide encoding a protein having of an amino acid sequence from N-terminal to an amino acid residue in position 692 in the entire amino acid sequence of the known bovine aggrecan shown in SEQ ID NO: 7" and which includes hyaluronic acid binding site. Namely, the polynucleotide of the present invention is the polynucleotide comprising the nucleotide sequence encoding the amino acid sequence in which leucine residue in position 131 from N-terminal in the known amino acid sequence of aggrecan is substituted by a residue derived from the other amino acid (i.e. amino acid sequences shown in SEQ ID NO: 2).

Namely, the polynucleotide of the present invention is "A polynucleotide encoding a protein having a hyaluronic acid binding ability comprising an amino acid sequence shown in SEQ ID NO: 2, wherein the amino acid sequence has an isoleucine residue in position 130 from N-terminal of the amino acid sequence, and a residue derived from an amino acid selected from the group consisting of tyrosine, serine, threonine, cysteine, asparagine and glutamine in position 131 from N-terminal of the amino acid sequence."

Among them, a polynucleotide encoding a polynucleotide encoding a protein comprising an amino acid sequence shown in SEQ ID NO: 2, wherein the amino acid sequence has an isoleucine residue in position 130 from N-terminal of the amino acid sequence, and a tyrosine residue position 131 from N-terminal of the amino acid sequence (i.e. an amino acid sequence shown in SEQ ID NO: 4), is preferable.

In addition, the polynucleotide of the present invention is similar to "a polynucleotide encoding a protein having an amino acid sequence from N-terminal to an amino acid residue in position 692 in the known entire amino acid sequence of bovine aggrecan, which includes hyaluronic acid binding site. Namely, in the case of the known nucleotide sequence of bovine aggrecan, a nucleotide sequence in positions 388 to 393 from 5' terminal, which encodes an amino acid residues (Ile-Leu) in positions 130 to 131 from N-terminal of the known amino acid sequence of bovine aggrecan, is "ATTCTA". In the case of the polynucleotide of the present invention, the sequence replaced from "ATTCTA" to another nucleotide sequence (i.e. the nucleotide sequence shown in SEQ ID NO: 1).

Namely, the polynucleotide of the present invention is "the polynucleotide encoding a protein comprising an amino acid sequence shown in SEQ ID NO: 2, wherein the polynucleotide comprises a nucleotide sequence shown in SEQ ID NO: 1; a base in position 390 from 5' terminal of the polynucleotide is the base selected from T, C and A; and bases in positions 391 to 393 from 5' terminal are nucleotide sequences selected from TAT, TAC, TCT, TCC, TCA, TCG, ACT, ACC, ACA, ACG, TGT, TGC, AAT, AAC, CAA and CAG (in this connection, A represents adenine, C represents cytosine, G represents guanine, and T represents thymine, respectively, and hereinafter same as above)".

In addition, as is clear from the nucleotide sequence shown in SEQ ID NO: 1, the nucleotide sequence in positions 388 to 389 in the polynucleotide of the present invention is "AT."

Among the polynucleotides of the present invention described above, a polynucleotide comprising of the nucleotide sequence shown in SEQ ID NO: 1, wherein the bases in positions 391 to 393 from 5' terminal of the polynucleotide are TAT is preferable.

Further, a polynucleotide consisting of a nucleotide sequence in which the bases in positions 391 to 393 from 5' terminal are TAT, and the base in position 390 from 5' terminal is C (i.e. the nucleotide sequence shown in SEQ ID NO: 3) is more preferable.

For comparison, a known nucleotide sequence encoding the amino acid sequence from N-terminal to the amino acid residue in position 692 in the known entire amino acid sequence having 2,327 amino acids of bovine aggrecan including hyaluronic acid binding site is shown in SEQ ID NO: 8. In addition, an amino acid sequence encoded by the nucleotide sequence (an amino acid sequence from N-terminal to the amino acid residue in position 692 including hyaluronic acid binding site in the known entire amino acid sequence of bovine aggrecan) is shown in SEQ ID NO: 9.

The HABP of the present invention is similar to "a protein having an amino acid sequence from N-terminal to an amino acid residue in position 692 in the known entire amino acid sequence of the above-described bovine aggrecan including hyaluronic acid binding site. Namely, in the case of the known amino acid sequence of bovine aggrecan, an amino acid residue in position 131 from N-terminal is leucine. In the case of the HABP of the present invention, the amino acid residue is replaced with other amino acid residue (i.e. amino acid sequence shown in SEQ ID NO: 2).

Namely, the HABP of the present invention is "A HABP comprising an amino acid sequence shown in SEQ ID NO: 2; an amino acid residue in position 130 from N-terminal of the amino acid sequence is isoleucine; an amino acid residue in position 131 is a residue derived from an amino acid selected from the group consisting of tyrosine, serine, threonine, cysteine, asparagine and glutamine."

Preferably, the HABP of the present invention includes a protein comprising an amino acid sequence shown in SEQ ID NO: 2, wherein an amino acid residue in position 131 from N-terminal is tyrosine residue (i.e. amino acid sequence shown in SEQ ID NO: 4).

Hereinafter, the present invention will be explained in detail.

I. Preparation of the Polynucleotide of the Present Invention

The polynucleotide of the present invention can be obtained by the known DNA synthesis method. For example, the polynucleotide can be obtained, for example, by using a DNA synthesizer, synthesizing a polynucleotide by the common phosphoamidite method, and purifying by the conventional methods using an anion exchange column chromatography, as commonly carried out in DNA synthesis.

In addition, the polynucleotide of the present invention can be obtained as a cDNA, which is obtained, for example, by extracting mRNA from animal tissues or the like, and synthesizing from the mRNA using the known method.

The mRNA for the synthesis of the HABP of the present invention can be obtained from animal cartilage tissue or the like such as nasal septum cartilage, bronchial cartilage, and the like.

Hereinafter, a method for preparing the polynucleotide of the present invention, for example, from animal cartilage tissue such as bovine nasal septum cartilage and the like, will be shown.

(1) Recovery of Total RNA

Firstly, after disrupting a tissue such as bovine nasal septum cartilage or the like by the conventional method, total RNA is extracted by the conventional method.

The conventional method includes, for example, a method for preparing total RNA by treating with guanidine thiocyanate, and then carrying out cesium chloride density-gradient centrifugation according to the method of Chirgwin et al., (Biochemistry, 18, 5294-5299, 1979); guanidine thiocyanate—hot-phenol method; guanidine thiocyanate—guanidine-hydrochloride method; guanidine thiocyanate—phenol-chloroform method; and the like.

In addition, since a variety of kits for obtaining total RNA are commercially available, those kits may be used. Such kits include, for example, RNeasy Lipid Tissue Midi Kit, RNeasy Lipid Tissue Mini Kit (product of QIAGEN GmbH.), and the like.

(2) Purification of mRNA

Purification of mRNA from total RNA may be carried out according to the conventional methods. The conventional methods include, for example, oligo(dT) cellulose column chromatography method purifying only mRNA in total RNA using a carrier which hybridizes to poly A tail of mRNA, lithium chloride/urea method, guanidine isocyanate method, and the like.

Also for purification of mRNA, since a variety of kits for this purpose are commercially available, those kits may be used. For example, Oligotex™-dT30<Super> (produced by Takara Bio Inc.) may be included.

(3) Preparation of cDNA and Cloning

By the conventional method using reverse transcriptase and polymerase chain reaction (PCR) using the obtained mRNA as a template, cDNA is synthesized and amplified. Commercially available kits for synthesis and cloning may be used.

For example, when PCR is carried out, a primer pair is designed based on the nucleotide sequence of the intended polynucleotide of the present invention, so as to replicate the part. Then, by carrying out PCR using the primer pair by the conventional method, the cDNA comprising the nucleotide sequence of the polynucleotide of the present invention which encodes the desired HABP of the present invention (i.e. polynucleotide comprising the nucleotide sequence shown in SEQ ID NO: 1 of the present invention), can be obtained.

(4) Determination of cDNA Nucleotide Sequence

Determination of the amplified cDNA nucleotide sequence may be performed by the conventional methods including cycle-sequencing method and the like.

II. Preparation of the HABP of the Present Invention (1) Production of the recombinant expression vector of the present invention, transfected host cell and transformant involved in the present invention.

The method for producing the HABP of the present invention is "a method for producing the protein comprising; culturing a host cell transfected by Baculovirus integrated with a recombinant expression vector having a polynucleotide comprising the nucleotide sequence shown in SEQ ID NO:1, or a transformant obtained by transforming the host cell by the recombinant expression vector, and separating and purifying a protein from the culture medium".

Namely, the HABP of the present invention can be obtained by the known process using the genetic recombination technique, that is, the polynucleotide of the present invention is integrated into an expression vector such as an appropriate plasmid or phage, the host cell is transfected or transformed using the expression vector, and the obtained host cell is cultured to elute the protein into or out of the cell.

The method generally used is a method using, an expression system using prokaryotic cell such as *Escherichia coli*, or an expression system using an eukaryotic cell such as common mammalian cell, yeast, insect cell and the like.

Among them, the expression system using a insect cell infected with Baculovirus is widely used in recent years, because the expression system is easy-to-use, and capable of obtaining the desired protein in a large quantity. Namely, Baculovirus has a character to produce a large number of inclusion bodies called polyhedra within a nucleus of the infected cell. The polyhedra comprises a protein called polyhedrin and the quantity of expression thereof is the to reach near a half of the total cellular protein. Therefore, a technique to conduct a synthesis of the recombinant protein within insect cells utilizing the very powerful promoter of the polyhedron gene is widely performed.

Also in the present invention, the expression system using the Baculovirus-insect cell may be used.

1) Method for Transfect a Host Cell Using the Baculovirus-Insect Cell System

Hereinafter, a method for obtaining the HABP of the present invention utilizing the expression system of Baculovirus-insect cell will be explained referring to an example, but the method is not limited particularly to this example, and the HABP of the present invention may be prepared using Baculovirus, insect cell, or the like commonly used in the art by the conventional method commonly used in the art.

The Baculovirus used for the expression system using Baculovirus-insect cell includes, the virus such as *Autographica californica* nuclear polyhedrosis virus, the virus infecting insects of *Mamestra* genus.

Insect cell used as the host cell includes Sf 9, Sf 20, or the like derived from *Spodoptera frugiperda*, High 5 derived from *Trichoplusia ni*, BTI-TN-5B1-4 (produced by Invitrogen Corp.), and the like.

When the polynucleotide of the present invention is integrated into Baculovirus, preferably, the polynucleotide is not integrated directly into Baculovirus, but as in the conventional method, the polynucleotide is first integrated into a transfer vector and subsequently co-transfected to the insect cell as a host together with Baculovirus genome DNA.

The transfer vector (to be used as the expression vector) includes vectors for insect cells such as pVL1392, pVL1393 and pBlueBacIII (these are produced by Invitrogen Corp.), pBacPAK9, AcNPV originated from *Autographa california* NPV, and the like.

Since the transfer vector has a polyhedrin promoter in front of the cloning site, the polynucleotide of the present invention is inserted into the downstream of the polyhedrin promoter gene by the conventional method. By this procedure, the recombinant expression vector involved in the present invention in which the polynucleotide of the present invention has been integrated can be obtained.

The transfer vector integrated with the polynucleotide of the present invention (recombinant expression vector) is co-transfected together with Baculovirus genome DNA into the insect cell as a host by the conventional method such as Calcium phosphate method (JP-A-2-227075), lipofection method (Proc. Natl. Acad. Sci., USA, 84, 7413, 1987), and the like. By the co-transfection, homologous recombination is induced at the polyhedrin site, and then a recombinant Baculovirus which is the polynucleotide of the present invention is introduced can be produced with high efficiency.

Three or four days after the co-transfection, the culture supernatant is recovered, and the recombinant Baculovirus is selected and purified from a mixture of recombinant and non-recombinant Baculovirus expressed in the culture medium by a conventional method such as limiting dilution method, plaque method, and the like. By the above-described procedures, "the recombinant Baculovirus" involved in the present invention integrated with "the recombinant expression vector" involved in the present invention can be obtained.

The obtained recombinant Baculovirus is infected (transfected) into the insect cell as a host. The transfection is carried out usually with 5 to 10 of MOI (Multiplicity of Infection). By the above-described procedures, the host cell involved in the present invention transfected with the recombinant Baculovirus involved in the present invention is obtained.

2) Method for Obtaining the Transformant of Host Cell

Also, besides the Baculovirus-insect cell expression system, the polynucleotide of the present invention can be expressed by the following method.

Firstly, the obtained cDNA is integrated into vector DNA according to, for example, the conventional method.

Expression vector is useful for the purpose for expressing the polynucleotide of the present invention to produce the HABP of the present invention.

The expression vector is not particularly limited, so long as it is capable of maintaining the replication or self-replicating ability within various kinds of host cells such as prokaryotic and/or eukaryotic cells, and has a function to express and produce the polynucleotide of the present invention. Such the expression vector includes plasmid vectors, phage vectors, virus vectors, and the like.

Such vector specifically includes, plasmid derived from *Escherichia coli* such as, for example, pUC119 (produced by Takara Shuzo Co. Ltd.), pQE-TRi plasmid (produced by QIAGEN GmbH.), pBluescript II KS+(produced by Stratagene Corp.), pBR322 (produced by Takara Shuzo Co. Ltd.), pGEM, pGEX, pUC, bpBS, pET, pGEM-3ZpMAL and the like; plasmids derived from yeast such as, for example, pB42AD, pESP, pESC, and the like; plasmids derived from *Bacillus subtilis* such as, for example, pHT926, pTB51, pHY481, and the like. Further, plasmids derived from mammalian cells such as pCAT3, pcDNA3.1, pCMV, and the like are also included.

In addition, phage includes bacteriophage including λ-phage such as XENBL 3 (produced by Stratagene Corp.), λDASHII (produced by Funakoshi, Co. Ltd.), λgt10, λgt11 (both are produced by TOYOBO Co. Ltd.), and the like, and cosmid vectors such as Charomid DNA (produced by Wako Pure Chemical Industries, Ltd.), Lorist 6 (produced by Wako Pure Chemical Industries, Ltd.), and the like, and so on.

Further, animal virus or insect virus such as retrovirus, vaccinia virus or Nuclear Polyhedrosis Virus is exemplified.

The recombinant expression vector integrated with the polynucleotide of the present invention can be prepared by integrating the polynucleotide of the present invention into the vector described above by the conventional method.

When bacteria, in particular *E. coli* is used for the host cell, generally the expression vector is composed of at least promoter-operator region, initiation codon, the polynucleotide of the present invention, termination codon, terminator region and units capable of replicating.

When yeast or animal cell is used as a host cell, the expression vector preferably comprises at least promoter, initiation codon, the polynucleotide of the present invention and termination codon. Also, a DNA encoding signal peptide, enhancer sequence, non-translation area in 5'- or 3'-terminal of the polynucleotide of the present invention, splicing junction or polyadenylation site may be integrated into the expression vector.

The promoter-operator region for expressing the polynucleotide of the present invention in bacteria includes the one comprising promoter, operator and Shine-Dalgarno (SD) sequence (for example, AAGG). For example, when host cell is a bacterium of *Escherichia* species, the region suitably includes the Tac promoter, Trc promoter, Trp promoter, lac promoter, rec A promoter, T7 promoter derived from bacteriophage, T3 promoter, SP6 promoter, λPL promoter, and the like.

The promoter for expressing the polynucleotide of the present invention in yeast includes ADH promoter, GAL1 promoter, and the like. When host cell is a bacterium of *Bacillus* genus, the promoter includes penP promoter, and the like. And when host cell is eukaryotic cell such as animal cell, SV40-derived promoter, CMV-derived promoter, promoter of retrovirus, heat shock promoter, polyhedrin promoter of nucleopolyhedrovirus, and the like are included. However, the promoter is not particularly limited to them. In addition, usage of an enhancer for expression is an effective method for expression.

As a suitable initiation codon, methionine codon (ATG) may be exemplified.

As a termination codon, the commonly used termination codon (for example, TAA, TAG, TGA, and the like) may be exemplified. The terminator region includes native or synthetic terminator.

The term "unit capable of replication" means a DNA having a function capable of replicating entire DNA sequence thereof in the host cell, and includes native plasmid, artificially modified plasmid (ex. DNA fragment prepared from native plasmid), synthetic plasmid, and the like.

As enhancer sequence, an enhancer sequence of major DNA virus such as CMV, SV40, polyoma, adeno, papilloma, and the like; an enhancer sequence of retrovirus Long Terminal Repeat (LTR); and an enhancer sequence of H chain gene or L chain gene of immunoglobulin may be exemplified.

The expression vector can be prepared by joining promoter, initiation codon, the polynucleotide of the present invention, termination codon and terminator region serially and circularly in an appropriate replicable unit. Also, in this occasion, a suitable DNA fragment (for example, linker, other restriction site, or the like) can be used by the conventional methods such as digestion with restriction enzyme, ligation using T4 DNA ligase, and the like, if necessary.

The transformant involved in the present invention can be prepared by inducing the above-described recombinant expression vector and the like into host cell.

The host cell includes, for example, microorganisms [bacteria (e.g. *Escherichia* genus and *Bacillus* genus), yeast (e.g. *Saccharomycetes* genus), animal cells insect cells, and the like]. Specifically, the host cell includes *Escherichia coli* (*Escherichia coli* BL21, BL21(DE3), DH1, DH5, DH5α, M15, HB101, C600, XL-1 Blue, JM109, JM105, JM127 or XL1-Blue) in *Escherichia* genus bacteria, and *B. subtilis, B. brevis* or *B. borstelenis* in *Bacillus* genus bacteria. The yeast includes *S. cerevisiae, Scizo. pombe, A. nidulans* and *Pichia pastoria*. Filamentous fungi of *Aspergillus* genus such as *Aspergillus nidulans*, and the like can also be used. The animal cell includes simian cell COS-7, Vero, Chinese hamster cell CHO, mouse L cell, human HeLa cell, FL cell and the like. The insect cell includes BmN4, Sf9, and the like. However, the host cell is not particularly limited to them.

Transformation or transduction of the host cells can be performed using the known methods. For example, transformation can be performed, for example, by calcium chloride method, electropolation method, rubidium chloride method, lipofection method, DEAE-dextran method, lithium method, spheroplast method, method using virus, or the like, and transduction can be performed, for example, by B. Hohn's method (Method in Enzymology, 68, 299-309, 1979), packaging method described in Meyerowitz, E. M., Gvild, G. H., Prestidge, L. S, and Honess, S. S., Gene, 11, 271 (1980), or the like.

(2) Culture of Host Cells

The HABP of the present invention can be produced by culturing host cell transfected by a virus having a recombinant expression vector integrated with the polynucleotide of the present invention obtained by the above-described method, or a transformant obtained by transforming the host cell with the recombinant expression vector in an appropriate medium suitable for the host cells (transformant), producing the HABP of the present invention in the culture, and separating the protein from the culture and purifying.

Preferably, the medium contains a carbon source, an inorganic nitrogen source or an organic nitrogen source, which are necessary for the growth of a host cell (transformant). The carbon source includes, for example, glucose, dextran, soluble starch, sucrose, and the like. The inorganic nitrogen source or organic nitrogen source includes, for example, ammonium salts, nitrate salts, amino acids, corn steep liquor, peptone, casein, meat extract, soymeal, potato extract, and the like. In addition, other nutrition (for example, calcium chloride, sodium dihydrogen phosphate or magnesium chloride), vitamins or antibiotics may be contained, if necessary.

The culture is performed by the method known in the art. Cultural conditions, for example, temperature, pH of medium and fermentation time are selected so as to obtain the highest titer of the HABP of the present invention.

In this connection, specific medium and cultural conditions are exemplified below, but the present invention is not limited thereto at all.

When the host cell is insect cells, the medium includes, for example, TNM-FH medium, Grace's Insectmedium [Proc. Natl. Acad. Sci. U.S.A., (1985) 82, 8404], Sf-100 II SFM medium (produced by Life Technologies, Inc.), ExCell 400 and ExCell 405 (both produced by JRH Biosciencies, Inc.). Alternatively, a medium which is added with fetal calf serum (FCS) or the like to these media may be used. Desirably, pH of the medium is 5 to 8.

The host cell transfected by the recombinant Baculovirus obtained above is cultured usually at 20 to 40° C., preferably at 25 to 30° C. for 12 hours to 10 days, and aeration or stirring may be carried out, if necessary.

When host cell is bacteria, *actinomyces*, yeasts or filamentous fungi, for example, a liquid medium containing the above-described nutrition sources is suitable. In this case, pH is desirably 5 to 8.

When host cell is *E. coli*, preferred medium for culture includes LB medium, 2YT medium, and Terrific Broth, M9 medium [Molecular Cloning, 3rd ed., appendix 2.2 (2001) Cold Spring Harbor Laboratory, New York] are exemplified. In this case, culture can be carried out usually at 14 to 42° C., preferably at 28 to 39° C. for about 3 to 24 hours, with aeration or stirring, if necessary.

When host cell is bacteria of *Bacillus* genus, culture can be carried out usually at 14 to 42° C., preferably at 28 to 39° C. for about 3 to 96 hours, with aeration or stirring, if necessary.

When host cell is yeast, the medium includes, for example, YPD medium (Molecular Cloning, 3rd ed., appendix 2.2 (2001) Cold Spring Harbor Laboratory, New York). The pH is desirably 5 to 8. Culture can be carried out usually at 14 to 42° C., preferably at 28 to 35° C. for about 12 hours to 10 days, with aeration or stirring, if necessary.

When host cell is animal cell, for example, MEM medium containing 5 to 20% FCS [Science, (1952) 122, 501], DMEW medium [Virology, (1959)8, 396], RPMI 1640 medium [J. Am. Med. Assoc., (1967) 199, 519], 199 medium [proc.

SSoc. Exp. Biol. Med., (1950) 73, 1], Daigo T2 medium (produced by Wako Pure Chemical Industries, Ltd.), and the like can be used as a medium. Preferably, pH of the medium is about 6 to 8, and culture can be carried out usually at 30 to 40° C., preferably at 34 to 38° C. for about 12 to 72 hours, with aeration or stirring, if necessary.

(3) Preparation of the HABP of the Present Invention.

Cells are removed from the culture obtained in the above-described (2) by carrying out a method such as filtration, centrifugation, or the like, and the culture filtrate or culture supernatant is recovered. After that, the HABP of the present invention is separated and purified from the culture filtrate or the culture supernatant according to the conventional methods usually used to separate and purify a native or synthetic protein.

Method for separation and purification of the HABP of the present invention includes, a known method utilizing solubility such as salting out method, solvent precipitation method, or the like; a method utilizing difference in molecular weight such as dialysis, ultrafiltration, gel filtration chromatography, sodium dodecylsulfate-polyacrylamide gel electrophoresis, and the like; a method utilizing electric charge such as ion-exchange chromatography, and the like; a method utilizing specific affinity such as affinity chromatography, and the like; a method utilizing difference in hydrophobic nature such as reverse phase high performance liquid chromatography, and the like; a method utilizing difference in isoelectric point such as isoelectric focusing electrophoresis, and the like; and so on.

On the other hand, when the HABP of the present invention is present in the periplasm or within the cytoplasma of the cultured transformant, cultured bacteria or cells are collected by subjecting the culture to the conventional method such as filtration, centrifugation, or the like, then suspended in a suitable buffer solution. After that, cell wall and/or cell membrane are disrupted by a method such as, for example, ultra-sonication, lysozyme treatment, freeze-and-thaw, and the like, and then, the crude extract containing the HABP of the present invention is obtained by a method such as centrifugation, filtration, and the like. And then, the HABP of the present invention can be separated from the crude extract and purified according to the conventional method exemplified above.

As an identification of the HABP of the present invention, western blot method, ELISA method, or the like, in which an antibody having reactivity to the HABP of the present invention is used as a probe.

The protein to be obtained in such way includes, for example, a protein having the amino acid sequence shown in SEQ ID NO: 2 or 4, In addition, the HABP of the present invention can be produced by a general chemical production method according to the amino acid sequence thereof. For example, the HABP of the present invention can be produced by a common chemical synthesis method such as fluorenylmethyloxycarbonyl method (Fmoc method), t-butyloxycarbonyl method (t-Boc method), and the like. Further, the protein can be chemically synthesized using a commercially available peptide synthesis equipment.

The method for measuring hyaluronic acid of the present invention includes, for example, a method by contacting hyaluronic acid in a sample with the HABP of the present invention to form a complex of hyaluronic acid and the HABP of the present invention, then reacting the complex with a carrier supporting an anti-HABP antibody, measuring an optical change by an agglutinate obtained from the reaction, and calculating an amount of the hyaluronic acid from the measured value.

In this connection, the measurement of the optical change described herein means the measurement of the optical change caused by the formation of immunoagglutination, and more specifically, in this category, immunoagglutination methods such as reversed passive agglutination method, nephelometric immunoassay and turbidimetric immunoassay are included. These measurement methods may be performed according to the method well known per se. When the reversed passive agglutination method is to be employed, the method may be carried out according to the procedure described, for example, in "Successive Course on Biochemical Experiment 5: Investigative Approach to Immunobiochemistry", Tokyo Kagaku Dojin Co., Ltd., pp. 36-37, "A Manual of Clinical Laboratory Method", $30^{th}$ ed., Kanehara & Co., Ltd., pp. 844-845, and when nephelometric immunoassay is to be employed, the method may be carried out according to the procedure described, for example, in "A Manual of Clinical Laboratory Test", 30th ed., Kanehara & Co., Ltd., pp. 851-853, and when turbidimetric immunoassay is to be employed, the method may be carried out according to the procedure described, for example, in "A Manual of Clinical Laboratory Method", $30^{th}$ ed., Kanehara & Co., Ltd., pp. 853-854.

An anti-HABP antibody to be used for the measurement of hyaluronic acid of the present invention may be either of a polyclonal antibody or a monoclonal antibody, so long as the antibody has reactivity to the HABP of the present invention. A polyclonal antibody purified by affinity-purification with single epitope, or a monoclonal antibody is preferable. A monoclonal antibody capable of binding efficiently with the HABP of the present invention is particularly preferable. Among them, the use of Fab, Fab', F(ab')$_2$ and the like produced by appropriate digestion of these antibodies using an enzyme such as pepsin and papain is preferable. When polyclonal antibody is used as anti-HABP antibody, the antibody can be prepared by a conventional method of immunization of an animal such as horse, cow, sheep, rabbit, goat, rat or mouse with the HABP of the present invention according to the methods described, for example, in "Matsuhashi, T. et al., Introduction to Experimental Immunology, $2^{nd}$ ed., 1981, Japan Scientific Societies Press". When monoclonal antibody is used as anti-HABP antibody, the antibody can be prepared according to a conventional method, namely, the cell fusion technology established by Kohler and Milstein (G. Kohler and C. Milstein: Nature, 256, 495 (1975)), for example, using a hybridoma cell obtained by fusing a cell line derived from mouse myeloma with cells from the mouse spleen which is preliminarily immunized with the HABP of the present invention. In addition, an antibody produced using a bovine aggrecan having a known amino acid sequence or a native bovine aggrecan as an antigen instead of the HABP of the present invention can be used as the "anti-HABP antibody" in the present invention.

As a carrier using for the measurement of hyaluronic acid, any one of carriers usually used in the immunological measurement can be adopted, specifically as preferable ones, carriers prepared from, for example, natural organic polymer substances such as red blood cell, bacteria, cell fragment and the like; assembly of molecule such as liposome, polymeric micelle and the like; synthetic polymer compounds such as polystyrene, polyacrylic acid, polymethacrylic acid, polyacrylamide, polyglycidylmethacrylate, polypropylene, polyvinylchloride, polyethylene, polychlorocarbonate, silicone resin, silicone rubber and the like; inorganic substances such as porous glass, ground glass, alumina, silica gel, activated carbon and metal oxide are included. In addition, these carriers can be used in various forms such as tube, bead, disc type chip, micro particle or latex particle. Among them, the latex particle is particularly preferable from the points, for example, that chemical treatment of the surface of the carrier can be easily carried out as appropriately for any purposes because the carrier material is artificial polymer and that nonspecific reaction hardly takes place. As to the quality of material, it has no specific limitation, but preferably includes, for example, styrene type latex particle such as polystyrene latex particle and acrylic acid type latex particle.

In this connection, among these latex particles, polystyrene latex particle and the like which are prepared by emulsion polymerization reaction without use of emulsifying agent are particularly preferable. Because, as they have a surface with strong hydrophobic nature, proteins or peptides can be adsorbed smoothly, and also as they have negatively charged surface and cause mutual repulsion between them, and they can stably disperse in a solution even in the absence of emulsifying agent. In addition, various modified latex particle (for example, a carboxylic acid modified latex particle produced by introducing carboxyl group into the above described polystyrene), a magnetic latex particle (a magnetic particle-encapsulated latex particle) and the like can be used as well.

In addition, as for latex particles to be used for the measurement of hyaluronic acid, commercially available latex with small average particle diameter, namely, with large surface area per unit weight, is able to support antibody efficiently and also provides a good storage stability (good dispersibility in a solution), and so, it is used preferably. In more specifically, the average particle diameter is usually 0.05 to 0.5 µm, preferably 0.1 to 0.4 µm. Using such latex particles with small average diameter, deposition of the particle can be avoided and it can be achieved to efficiently support anti-HABP antibody on the latex particles. That is, by the use of such anti-HABP antibody-supported latex particles, both the increased stability of the measurement reagent and high accuracy of measurement can be achieved.

The method of supporting the above-described anti-HABP antibody on the above-described carrier may be performed without specific limitation by contacting the anti-HABP antibody with the carrier. All the supporting methods well known per se usually used in this field can be included, and for example, as an exemplary method, method of supporting the anti-HABP antibody on the carrier by physical adsorption, so called physical adsorption method (refer to, JP-A-1993-41946; SUMILON Technical Report, SUMILON ELISA series 1 Introduction to ELISA Method, published by Sumitomo Bakelite Co., Ltd.; SUMILON Technical Report, SUMILON ELISA series 2 Solid Phase Surface of ELISA Products, published by Sumitomo Bakelite Co., Ltd., and so on) is included as representative examples. The above-described method is usually used as a preferable method when, for example, synthetic polymer compounds such as polystyrene, polypropylene, polyvinylchloride, polyethylene, polychlorocarbonate and the like; activated carbon; inorganic substances such as porous glass, ground glass, alumina, silica gel, metal oxide hydroxyapatite and the like are used as a carrier. Among them, it is particularly preferable when glass, polystyrene, polyvinylchloride and the like are used in the form of, for example, tube, bead, disc chip, micro particle or latex particle.

In addition, when a commercially available carrier is used, the anti-HABP antibody may be supported on a carrier according to the supporting method recommended in the instruction thereof.

Taking a case as an example when an anti-HABP antibody is supported on the latex particles, the latex particles are added so as to be concentration of usually 0.1 to 10% (w/v), preferably 0.2 to 5% (w/v) and suspended in a solvent such as a buffer solution containing usually 0.05 to 2 mg/ml, preferably 0.1 to 1 mg/ml of an anti-HABP antibody, and after reacting usually at 5 to 30° C. and usually for 2 to 3 hours, then, post treatments usually conducted in this field such as, for example, centrifugation, blocking treatment using a solution containing an appropriate protein such as bovine serum albumin (BSA) are carried out, and thus work up the supporting process. In this connection, it can also be achieved to support the anti-HABP antibody on a carrier by chemical binding methods usually used in this field.

Taking the turbidimetric immunoassay using latex particle carrier as an example, the method for measuring hyaluronic acid using the HABP of the present invention will be described more specifically below. That is, a sample containing hyaluronic acid (more specifically, for example, body fluid such as blood, plasma, serum, synovial fluid, pleural fluid, lymph fluid, spinal fluid and urine) is contacted and mixed with a reagent containing above described HABP to form hyaluronic acid/HABP of the present invention complex. Then, for example, a reagent, wherein above described anti-HABP antibody is supported (sensitized) on latex particles with average particle diameter of, for example, 0.05 to 0.5 µm, preferably 0.1 to 0.4 µm, is reacted with above described complex. The degree of resulting agglutination is measured, for example, by means of absorbance, and the concentration is determined from a calibration curve preliminarily prepared using standard sample, and thus, the quantity of hyaluronic acid in a sample is assayed.

In this connection, the method for measuring the absorbance may be carried out usually at wavelength of 340 to 1000 nm, preferably at 500 to 900 nm. In addition, determination of the degree of agglutination is not limited to the measurement of absorbance; the degree may be measured by any one of the methods well known per se, for example, by nephelometry or by counting immunoassay. In addition, when the hyaluronic acid/HABP of the present invention complex is reacted with a reagent containing an anti-HABP antibody which has been supported on a carrier such as latex particles (hereinafter, may referred to as anti-HABP antibody-supported carrier), appropriate agglutination accelerating agent may be added.

In the method for measuring hyaluronic acid using the HABP of the present invention, the use concentration of HABP of the present invention in HABP reactions is, although it may vary depending on the detection limit of hyaluronic acid be set out, usually, equal to or more of the concentration which is capable of binding with all amount of hyaluronic acid corresponding to the set concentration of detection limit, preferably 5 times or more, more preferably 10 times or more of the set concentration of determination limit In this connection, the upper limit concentration of hyaluronic acid on this occasion has no limitation, in consideration of economical amount of the hyaluronic acid, the concentration is usually 50,000 times or less, preferably 10,000 times or less. Specifically, the concentration is usually from 0.1 to 1000 µg/ml, preferably from 0.5 to 1000 µg/ml, and more preferably from 0.5 to 100 µg/ml. For example, when hyaluronic acid concentration in serum is measured, as usual determination limit is from 10 to 1000 ng/ml, the use concentration of HABP of the present invention in HABP reaction may, therefore, be set out appropriately within the above-described range based on the determination limit.

In addition, as to the pH in the reaction, the range thereof is not specifically limited as long as it does not inhibit formation of the complex, and is usually 5 to 10, preferably 6 to 8. Also, as to the temperature in the reaction, the range thereof is not specifically limited as long as it does not inhibit the formation of the complex, and is usually 5 to 40° C. In addition, the reaction may be conducted for several seconds to several hours as appropriate according to each condition.

In the method for measuring hyaluronic acid using the HABP of the present invention, the use concentration of anti-HABP antibody-supported carrier in the reaction between ant HABP antibody-supported carrier and hyaluronic acid/HABP of the present invention complex is, while it may vary depending on the use concentration of HABP of the present invention in the above reaction, usually 0.2 to 25 mg/ml, preferably 0.5 to 12 mg/ml when latex particles having 0.01 to 0.1 mg/mg of supporting amount of anti-HABP antibody is used, and, if it is within the range of the above-described concentration, the hyaluronic acid in a sample can be measured with a high degree of accuracy. In this connection, the condition and the time for the reaction of anti-HABP antibody-supported carrier with hyaluronic acid/HABP of the present invention complex may be conducted according to those when the HABP of the present invention is reacted with hyaluronic acid.

The reagent kit for measuring hyaluronic acid of the present invention is the one comprising the HABP of the present invention as a constituent.

In addition, the kit may contain a reagent comprising the anti-HABP antibody-supported carrier. Further, the kit may contain a standard substance usually used in this field such as, for example, potassium hyaluronate (derived from cockscomb, produced by Wako Pure Chemical Industries, Ltd.) and sodium hyaluronate (derived from *Streptococcus* species, produced by Wako Pure Chemical Industries, Ltd.).

The HABP comprising in the reagent kit for the measurement of hyaluronic acid of the present invention may be a reagent comprising HABP of the present invention, and may be dissolved the HABP of the present invention in an appropriate buffer solution. As the buffering agents used for this purpose, any kind of buffering agent usually used in the immunological measurement, for example, Tris buffering agent, phosphate buffering agent, veronal buffering agent, boric acid buffering agent and Good buffering agent can be adopted, and the concentration of such buffering agent is usually 5 to 300 mM, preferably 10 to 150 mM, and the pH is usually 5 to 10, preferably 6 to 8, and the concentration and pH are each selected appropriately from above described corresponding range.

As to the concentration of HABP of the present invention in the above reagent comprising HABP of the present invention, the concentration in the reaction may be set out to be the same concentration as described above, and may be selected appropriately so as to be within the range from 0.1 to 500 µg/ml, preferably 0.5 to 100 µg/ml.

The reagent comprising the anti-HABP antibody-supported carrier in the reagent kit for measurement of hyaluronic acid of the present invention may be the one which comprises the above-described anti-HABP antibody-supported carrier. The reagent is the one in which the anti-HABP antibody-supported carrier is suspended in a suitable buffer solution or lyophilized one thereof. The buffering agent to be used for this purpose may be any kind of buffering agent so long as it does not have a character to disturb the binding of the anti-HABP antibody involved in the present invention with the HABP of the present invention, and includes the same buffering agents for the above-described reagent comprising the HABP of the present invention. Similarly, pH and concentration thereof may be also set according to the above-described values.

In addition, the reagent comprising an anti-HABP antibody-supported carrier is provided in many cases in the form of suspension suspended in a solution such as buffer solution. As the buffer solution used for preparing such suspension, any one usually used in this field is adopted without specific limitation, and usually one having buffering action at pH 5.0 to 10.0, preferably around neutral pH of pH 6.5 to 8.5, for example, phosphate buffer, Tris buffer or Good buffer is preferable. In this connection, depending on the characteristics of the insoluble micro particles, some one has a tendency to make aggregation naturally by leaving in suspended condition. In such case, the use of a mildly alkaline buffer solution such as glycine buffer or boric acid buffer for the preparation of suspension is far more preferable from a standpoint of storage stability. In addition, the concentration of buffering agent in these buffers is selected appropriately from the range of usually 10 to 500 mM, preferably 10 to 300 mM. In this connection, in the reagent, for example, a stabilizing agent such as a sugar, a protein and a surface activating agent, a salt such as NaCl and an preservative substance and the like may be added within the range usually used in this field.

When the anti-HABP antibody-supported carrier involved in the present invention is suspended in an above described buffer solution, the concentration of the anti-HABP antibody-supported carrier in the reaction may be, while it may vary depending on the kind of anti-HABP antibody used, set out to be the same concentration as described above, and may be selected appropriately so as to be usually within a range from 0.1 to 100 mg/ml, preferably from 2 to 50 mg/ml.

Further, in the reagent comprising an anti-HABP antibody-supported carrier involved in the present invention, an immunological reaction accelerator (agglutination reaction accelerator) (for example, polyethylene glycol and polyvinyl alcohol) may coexist at the concentration range usually used in this field, and even under coexistence of such agglutination reaction accelerator, the appearance of nonspecific turbidity of denatured protein constituent in the measuring reagent, which is caused by some sort of factor, can be repressed or reduced by the method of the present invention. In addition, a monomer or a polymer used as an agglutination accelerator described in JP-A-2002-365296 may be contained as an agglutination accelerator in the above-described reagent, and the concentration range thereof may be selected according to the value described in JP-A-2002-365296. In this connection, the monomer or polymer may be prepared according to the method described in the above patent application.

As to a sample involved in the present invention, any sample containing hyaluronic acid may be adopted, and specifically, it includes, for example, body fluid such as blood, plasma, serum, synovial fluid, pleural fluid, lymph fluid, spinal fluid and urine, and as preferable sample among them, serum, urine and the like are included.

Hereinafter, the present invention will be explained more specifically referring to Examples, but the present invention is not limited thereto by no means.

Example 1

(1) Recovery of RNA

Total RNA was recovered from bovine cartilage of nasal septum using RNeasy Lipid Tissue Kit produced by QIAGEN GmbH according to the protocol of the kit as described below.

Firstly, bovine cartilage of nasal septum (produced in New Zealand) (1 g) was added in a tube containing QIAzol Lysis Reagent (5 mL) accompanying to the kit, and the tissue was disrupted using Polytron homogenizer.

After incubating the obtained homogenate at room temperature for 5 minutes, chloroform (1 mL) was added thereto. The mixture was stirred for 15 second, and further incubated at room temperature for 3 minutes. After that, the homogenate was centrifuged at 4° C. at 5,000×G for 15 minutes, then water phase was transferred to a new tube, and equal volume of 70% ethanol was added thereto. After stirring, the obtained solution (3 mL) was transferred to the RNeasy Midi Spin Column set to the collection tube (15 ml) accompanying to the kit, and the column was centrifuged at 25° C. at 3,000×G for 5 minutes. By this procedure, the total RNA bound to the membrane of RNeasy Midi Spin Column. Then, the Buffer RW1 (4 ml) accompanying to the kit was added to the column, and centrifuged at 25° C. at 3,000×G for 5 minutes. After that, Buffer RPE (2.5 mL) was added and centrifuged at 25° C. at 3,000×G for 2 minutes. Further, Buffer RPE (2.5 mL) was added and centrifuged at 25° C. at 3,000×G for 5 minutes.

The obtained RNeasy Midi Spin Column having bound total RNA was transferred to a new collection tube. Sterilized water (150 μL) was added to the membrane of RNeasy Midi Spin Column, and the column was centrifuged at 25° C. at 3,000×G for 3 minutes, and this procedure was repeated twice to elute total RNA from the membrane. Absorbance of the obtained eluate was measured to confirm that 500 μg of total RNA was recovered from 1 g of bovine cartilage of nasal septum.

Electrophoresis was carried out with the recovered total RNA solution (5 μL) on 1% agarose gel.

The results obtained is shown in FIG. 1.

As is clear from FIG. 1, clear bands of 18s rRNA and 28s rRNA could be identified, and it was confirmed that total RNA could be recovered without decomposition by the above-described method.

(2) Purification of mRNA

Using Oligotex™-dT30<Super> (produced by Takara Bio, Inc.), mRNA was purified by the following method.

Firstly, Elution Buffer (accompanying to the kit) (250 μL) was added to aqueous solution of total RNA (250 μL) obtained in above (1), and further Oligotex™-dT30 (500 μL) was added thereto. The solution was incubated at 65° C. for 5 minutes, after that the reaction solution was left on ice for 3 minutes. To the reaction solution, 5M NaCl (0.1 mL) was added, and the solution was incubated at 37° C. for 10 minutes. The reaction solution was centrifuged at 15,000 rpm for 3 minutes, the supernatant was removed and pellet was dissolved in TE (Tris-EDTA buffer, pH8.0) (450 μL). After that, the solution was incubated at 65° C. for 5 minutes and left on ice for 3 minutes. After that, the solution was centrifuged at 15,000 rpm for 3 minutes and the supernatant (400 μL) was recovered. After the conventional ethanol precipitation treatment, the precipitant was dissolved in TE (10 pt) to obtain a solution of purified mRNA.

(3) Preparation of cDNA and PCR Cloning

Synthesis of cDNA was carried out by PCR using the purified mRNA obtained in above (2) as described below.
1) Primer Based on the known genetic sequence of *Bos Taurus* aggrecan that has been disclosed in the DDBJ (DNA Data Bank of Japan) database, the following primer sequences were designed and synthesized by the conventional synthesis method. The primers have a sequence corresponding to a part of the known nucleotide sequence encoding the amino acid sequence from N-terminal to the position 692 including the above-described known hyaluronic acid binding site of *Bos Taurus* aggrecan. In addition, in primer F and primer R, a nucleotide sequence encoding the amino acid sequence of the restriction enzyme site of EcoRI is inserted, and further, termination codon is added in primer R.

```
Primer sequences
                                              (SEQ ID NO: 5)
primer F        atgaattcatgaccactttactcttggtgtttg (SEQ ID NO: 6)
primer R        atgaattctcatggagagggcgccgctgaaacacc
```

2) PCR

Using a combination of the above-described primers and the purified mRNA obtained in above (2) as a template, cDNA having a sequence similar to the known nucleotide sequence which encodes the amino acid sequence from N-terminal to the position 692 including the known hyaluronic acid binding site of *Bos Taurus* aggrecan was amplified by the conventional method for replication of cDNA from mRNA by PCR.

PCR was carried out under the following reaction conditions. After heating at 98° C. for 2 minutes, 30 cycles of 95° C. for 15 seconds, 63° C. for 30 minutes, and 68° C. for 2 minutes were repeated, and finally treatment at 68° C. for 5 minutes was carried out.

Reaction Condition of PCR:

| | |
|---|---|
| Sterilized water: | 71 μL |
| RNA solution: | 1 μL |
| Primer F: | 1 μL |
| Primer R: | 1 μL |
| MgCl$_2$ : | 4 μL |
| dNTP (the mixture of dATP, dGTP, dCTP, dTTP): | 10 μL |
| Buffer solution: | 10 μL |
| KOD: | 2 μL |

The obtained PCR product contains a nucleotide sequence of restriction enzyme site of EcoRI. Therefore, the PCR product was digested and cut at this restriction enzyme site.

The fragment of PCR product obtained was subjected to an electrophoresis on 1% agarose Gel containing 1 μg/ml ethidium bromide.

Results are shown in FIG. 2. In FIG. 2, lane 1 shows the result when DNA Marker 6 (λ/Sty I, produced by Nippon Gene, Co., Ltd.) which is a marker of molecular weight was used as a sample, and lane 2 shows the result when fragment of PCR product was used as a sample. In addition, the arrow shows a fraction of the fragment of PCR product.

As is clear from FIG. 2, a main band was identified at the position of about 2,100 bp (the fraction indicated with the arrow in FIG. 2).

This fraction was cut out, and the fragment of PCR product was purified using GENEPURE (produced by Nippon Gene, Co., Ltd.).

(4) Preparation of Recombinant Vector and Determination of Nucleotide Sequence

After that, using Baculogold Starter Kit (produced by Becton Dickinson & Co.), a recombinant vector was prepared, by splicing the fragment of PCR product prepared in the above (3) to EcoRI site which is in the downstream of polyhedrin promoter of pVL1392 transfer vector for insect cell accompanying to the Kit. Since the obtained recombinant vector was inserted with the same nucleotide sequence as cDNA obtained in the above (3)2), hereinafter, the recombinant vector obtained will be described as "pVL1392/cDNA".

Using recombinant vector pVL1392/cDNA (200 ng) as a template and a combination of primers used in the above (3)1), PCR was carried out using DYEnamic ET Terminator Cycle Sequencing Kit (produced by GE Healthcare Life Sciences, Co.) according to the method described in the accompanying manual to obtain a PCR product.

(5) Homology Search of Nucleotide Sequence

Decoding of the obtained PCR product (having the same nucleotide sequence as cDNA obtained in the above (3)) was carried out using BaseStation (produced by Biorad Laboratories, Inc.).

After that, homology search (BLAST) for nucleotide sequence of the obtained PCR product was carried out using DDBJ (DNA Data Bank of Japan) database. As a result, it was revealed that the nucleotide sequence of the obtained PCR product, i.e. the nucleotide sequence of cDNA, showed high homology to the known gene sequence of *Bos Taurus* aggrecan.

Namely, in the known gene sequence of *Bos Taurus* aggrecan, the bases encoding an amino acid in positions 129 to 130 from N-terminal (Ile-Leu) were "ATTCTA", while the bases of the obtained cDNA at the corresponding position, that is, in positions 388 to 393 were "ATCTAT". Nucleotide sequence in other part was found to be identical to each other.

From the above-described facts, it was confirmed that the nucleotide sequence of cDNA obtained in the above (3) was the sequence shown in SEQ ID NO: 3, and the recombinant vector (pVL1392/cDNA) obtained in the above (4) was a recombinant vector in which the cDNA was integrated.

In addition, the amino acid sequence encoded by the nucleotide sequence of SEQ ID NO: 3 estimated from the nucleotide sequence shown in SEQ ID NO: 3 is the amino acid sequence consisting of 692 amino acids in the total length shown in SEQ ID NO: 4. The amino acid sequence was compared with the known entire sequence of 2,327 amino acids of the *Bos Taurus* aggrecan. As a result, in the known amino acid sequence of the *Bos Taurus* aggrecan, an amino acid in position 131 from N-terminal was leucine, whereas an amino acid in position 131 from N-terminal of the amino acid sequence shown in SEQ ID NO: 4 was tyrosine. As to amino acid sequences in other part, a sequence from N-terminal to an amino acid residue in position 692 in the entire 2,327 amino acids of the known *Bos Taurus* aggrecan and an amino acid sequence shown in SEQ ID NO: 4 were identical.

(6) Preparation of Baculovirus

Baculovirus integrated with cDNA was prepared by the following method using Baculogold Starter Kit (produced by Becton Dickinson & Co.).

Firstly, a linearized Baculovirus DNA (modified *Autographa californica* nuclear polyhedrosis virus: AcNPV) (0.5 μg) accompanying to, the Kit was mixed with the recombinant vector pVL1392/cDNA obtained in the above (4), and left at room temperature for 5 minutes, and then mixed with Buffer B (1 mL) to make a DNA solution.

In TNH-FH medium (4 mL) containing 10% FCS, sf9 cell was cultured, and the medium was substituted by Buffer A (1 mL), and cell content was adjusted to $2 \times 10^6 / 25$ cm$^2$. The DNA solution (1 mL) prepared as described above was dropped thereto, and the mixture was incubated at 27° C. for 4 hours as it is to perform co-transfection. After that, the sf9 cells were washed with new TNM-FH medium and the TNM-FH medium (3 mL) was added newly, and the mixture was cultured for 3 days.

Since the recombinant virus in which the recombinant vector pVL1392/cDNA was integrated into the genome DNA thereof bud to culture, after culturing sf9 cells for 3 days, the culture medium was recovered.

(7) Expression of HABP of the Present Invention

Number of the recombinant virus in the culture medium obtained in the above (6) was examined by the conventional plaque assay method.

After that, the recombinant virus was transfected into the sf9 cells at MOI of 5, and incubated in Grace's Insect Medium containing 10% FCS at 27° C. for 4 days.

After the culture, the culture medium was centrifuged and the culture supernatant obtained was recovered. After that, the culture supernatant was subjected to an affinity chromatography using Aggrecan antibody column to purify the protein.

In this connection, the Aggrecan antibody column used was prepared by the recommended method accompanying to the carrier (shown in following (2)), (1) using anti HABP monoclonal antibody prepared by the conventional method, using the Aggrecan (produced by Seikagaku Corp.) which was purified from bovine cartilage of nasal septum by the modified Laurant's method as an antigen, and (2) using NHS-activated Sepharose 4 fast flow (produced by GE Healthcare-Biosciences) as a carrier.

Production of HABP of the present invention was identified by Western blotting technique in the following procedures.

SDS-PAGE procedures were carried out using the culture supernatant before the affinity purification, the culture supernatant after the affinity purification, and the protein obtained by affinity purification as samples, respectively, and each of them was transferred to PVDF membrane. After blocking treatment of the PVDF membrane, the membrane was reacted with peroxidase-labeled anti-Aggrecan antibody at room temperature for 1 hour. After washing the PVDF membrane with PBS-T for 3 times, the membrane was made luminescent using ECLplus (produced by GE Healthcare-Biosciences), and an UV film was exposed thereto.

In this connection, the peroxidase-labeled anti-Aggrecan antibody used as described above was the one in which the same anti-Aggrecan monoclonal antibody as used for the Aggrecan antibody column used in the above-described affinity chromatography was labeled with green horseradish peroxidase by the conventional method.

In addition, the gel after SDS-PAGE was subjected to silver stain according to the conventional method.

Results are shown in FIG. 3. In FIG. 3, (*a*) shows the result of the silver staining of the gel after the SDS-PAGE, and (*b*) shows the result of Western blotting using peroxidase-labeled anti-Aggrecan antibody, respectively.

In addition, in (a) and (b) of FIG. 3, results are shown when the following materials were used as a sample, respectively: lane 1: the molecular weight marker of protein, Precisionplus Protein Standard (BIO-RAD), lane 2: the culture supernatant before affinity purification, lane 3: the culture supernatant after affinity purification, and lane 4: the protein obtained by affinity purification. In addition, the arrow in FIG. 3(*b*) indicates a fraction of the HABP of the present invention.

As is clear from the comparison the results of (a) and (b) in FIG. 3, a fraction crossed with peroxidase-labeled anti-Aggrecan antibody was detected in the culture supernatant before affinity purification (lane 2), whereas a fraction crossed with peroxidase-labeled anti-Aggrecan antibody was not detected in the culture supernatant after affinity purification (lane 3). In addition, in a purified protein fraction obtained by eluting affinity carrier with eluting buffer solution (lane 4), a fraction crossed with peroxidase-labeled anti-Aggrecan antibody was detected.

In addition, size of the protein in the fraction crossed with the Aggrecan antibody identified by SDS-PAGE was about 90 kDa, and was larger than the molecular weight estimated from the amino acid sequence of known Bos Taurus aggrecan which had been disclosed in the database, and therefore, it was presumed that a sugar chain is added to the obtained protein.

From the above results, it was confirmed that the expressed protein was a protein crossed with the anti-Aggrecan antibody.

Therefore, it was confirmed that the desired HABP of the present invention could be expressed by the methods described above.

Example 2

Measurement of Hyaluronic Acid-1 (Preparation of Standard Curve)

(1) Preparation of Reagents
1) Preparation of First Reagent (Containing the HABP of the Present Invention)

The HABP of the present invention (100 µg) after the purification by affinity chromatography obtained in Example 1 (7) was dissolved in 100 mM HEPES buffer solution (containing 0.1% BSA and 1% NaCl, pH 7.0) (10 mL) to make a first reagent.

2) Preparation of Second Reagent (Latex Particles Sensitized by the Monoclonal Anti-HABP Antibody)

Purified water (800 µL), Latex particles solution (produced by Sekisui Chemical Co., Ltd., E05K29S, 10% by weight, diameter of latex particle: 0.3 µm) (100 µL), 500 mM borate buffer solution (pH 7.3) (100 µL), 50 mM ASES buffer solution containing monoclonal anti-HABP antibody (concentration of the monoclonal anti-HABP antibody: 4.24 mg/ml, pH6.5) (100 µL) were added in a 2 ml polycarbonate centrifugation tube, and the mixture was incubated at room temperature for 100 minutes with stirring to obtain a suspension of monoclonal anti-HABP antibody-supported latex particles. Concentration of monoclonal anti-HABP antibody in the incubation was about 0.385 mg/mL.

In addition, the above-described monoclonal anti-HABP antibody was the one which was prepared by the conventional method using hyaluronic acid binding protein purified from bovine cartilage of nasal septum by the modified method of Laurant et al. (produced by Seikagaku Corp.) as an antigen.

After that, the obtained suspension of monoclonal anti-HABP antibody-supported latex particles was centrifuged at 15,000 rpm for 15 minutes. The supernatant was removed, and 50 mM borate buffer solution (containing 2.5% BSA, pH 7.3) (1 ml) was added to the pellet on the bottom of the tube. The pellet was subjected to ultrasonic treatment under ice-cooling for 1 minute, and suspended again. The suspension was incubated at room temperature for 120 minutes with stirring, and the area on the surface of latex particle where the antibody was not supported was covered with BSA.

After that, the suspension of the latex particles was centrifuged at 15,000 rpm for 15 minutes. The supernatant was removed, and 50 mM borate buffer solution (containing 0.5% BSA, pH 7.3) (1 ml) was added to the pellet on the bottom of the tube. After that, the pellet was suspended again by applying ultrasonic treatment for 1 minute with ice-cooling, and diluted by 3.33-fold with 50 mM borate buffer solution (containing 2.5% BSA, pH 7.3), to make a second reagent.

3) Preparation of Hyaluronic Acid Solutions

Sodium hyaluronate (produced by Kibun Food Chemifa Co., Ltd.) was diluted with 50 mM phosphate buffer solution (pH 7.0) so as to obtain concentrations in hyaluronic acid solution of 50, 100, 200, 500 and 1,000 ng/mL, to make a hyaluronic acid solutions.

(2) Measurement of Hyaluronic Acid

Using the hyaluronic acid solutions prepared in the above (1) 3) as a sample, absorbance at 805 nm of each sample was measured with a full automatic measurement system (JEOL Ltd., Model BM-8) under the following measurement conditions.

Sample: 2.4 µL
First reagent: 90 µL
Second reagent: 30 µL
Measurement method: 2 point-end method
Main wavelength: 805 nm Concentration of the HABP of the present invention in the measurement was about 7.35 µg/mL.

(3) Results

Results obtained are shown in FIG. 4 (-○-).

Value on the longitudinal axis in FIG. 4 is a value obtained by subtracting blank value (an absorbance when concentration of hyaluronic acid was 0) from an absorbance obtained by the measurement, and multiplying by 10,000.

Comparative Example 1

(1) Preparation of Reagent

1) Preparation of First Reagent (Containing Native HABP)

Hyaluronic acid binding protein (purified from bovine cartilage of nasal septum by the modified method of Laurant, et al, produced by Seikagaku Corp., hereinafter, referred to as "native HABP") (20 µg) was dissolved in 100 mM HEPES buffer solution (containing 0.1% BSA and 1% NaCl, pH 7.0) (10 mL), to make a first reagent.

2) Preparation of Second Reagent (Latex Particles Sensitized by Monoclonal Anti-HABP Antibody)

The same second reagent as prepared in Example 2 (1)2) was used.

3) Preparation of Hyaluronic Acid Solution

The same hyaluronic acid solution as prepared in Example 2 (1)3) was used.

(2) Measurement of Hyaluronic Acid

Using the hyaluronic acid solution prepared in the above (1)3) as a sample, an absorbance at 805 nm of each sample was measured with the same equipment and by the same method as in Example 2 (2).

Concentration of native HABP in the measurement was about 1.47 µg/mL.

(3) Results

Results obtained are shown with (-♦-) in FIG. 4 together with results of Example 2.

As is clear from the results in FIG. 4, as a result of performing the measurement of hyaluronic acid using the HARP of the present invention, a superior standard curve same as in the case when conventional native HABP was used was obtained. From these results, it can be understood that measurement of hyaluronic acid can be performed using the HABP of the present invention.

Example 3

Measurement of Hyaluronic Acid-2 (Effect of Prozone Phenomenon)

(1) Preparation of the Reagent

1) Preparation of First Reagent (Containing the HABP of the Present Invention)

The HABP of the present invention (100 µg) after the purification by affinity chromatography obtained in Example 1 (7) was dissolved in 100 mM HEPES buffer solution (containing 0.1% BSA and 1% NaCl, pH 7.0) (10 mL), to make a first reagent.

2) Preparation of Second Reagent (Latex Particles Sensitized by Monoclonal Anti-HABP Antibody)

The same second reagent as prepared in Example 2 (1)$_2$) was used.

3) Preparation of High Concentration Hyaluronic Acid Solution

Sodium hyaluronate (produced by Kibun Food Chemifa Co., Ltd.) was diluted with 50 mM phosphate buffer solution (pH 7.0) so as to obtain concentrations in high concentration hyaluronic acid solution of 5,000, 10,000, 20,000, 50,000, 100,000, 200,000, 500,000, and 1,000,000 ng/mL, to make a high concentration hyaluronic acid solutions.

(2) Measurement of Hyaluronic Acid

Using the hyaluronic acid solutions prepared in the above (1) 3) as a sample, absorbance at 805 nm of each sample was measured with a full automatic measurement system (JEOL Ltd., Model BM-8) under the following measurement conditions.

Sample: 2.4 µL,

First reagent: 90 µL

Second reagent: 30 µL

Measurement method: 2 point-end method

Main wavelength: 805 nm

Concentration of the HABP of the present invention in the measurement was about 7.35 µg/mL (3) Results Results obtained are shown in FIG. 5 (-○-).

In addition, results of the measurements using the samples in which concentrations of hyaluronic acid in the hyaluronic acid solution were 50, 100, 200, 500 and 1,000 ng/mL obtained in Example 2 are shown together in FIG. 5 (-○-).

Value on the longitudinal axis in FIG. 5 is a value obtained by subtracting blank value (an absorbance when concentration of hyaluronic acid was 0) from an absorbance obtained by the measurement, and multiplying by 10,000.

Comparative Example 2

(1) Preparation of Reagents

1) Preparation of First Reagent (Containing Native HABP)

Native HABP (produced by Seikagaku Corp.) (20 µg) was dissolved in 100 mM HEPES buffer solution (containing 0.1% BSA and 1% NaCl, pH 7.0) (10 mL), to make a first reagent.

2) Preparation of Second Reagent (Latex Particles Sensitized by Monoclonal Anti-HABP Antibody)

The same second reagent as prepared in Example 3(1)2) was used.

3) Preparation of High Concentration Hyaluronic Acid Solution

The same high concentration hyaluronic acid solution as prepared in Example 3(1) 3) was used.

(2) Measurement of Hyaluronic Acid

Using the hyaluronic acid solution prepared in the above (1)$_3$) as a sample, an absorbance at 805 nm of each sample was measured with the same equipment and by the same method as in Example 3(2).

Concentration of native HABP in the measurement was about 1.47 µg/mL.

(3) Results

Results obtained are shown with (-♦-) in FIG. 5 together with results of Example 3.

As is clear from FIG. 5, when the measurement was carried out at antigen excess zone, the degree of decrease of absorbance caused by prozone phenomenon obtained by the measurement using the HABP of the present invention was smaller than that obtained by the measurement using the conventional native HABP.

From the results described above, it can be understood that when concentration of hyaluronic acid is measured using the HABP of the present invention, a high-precision measurement of hyaluronic acid concentration can be performed even at an antigen excess zone.

Example 4

Measurement of Hyaluronic Acid-3

(1) Preparation of Reagent

1) Preparation of First Reagent (Containing the HABP of the Present Invention)

The HABP of the present invention after the purification by affinity chromatography obtained in Example 1(7) was dissolved in 100 mM HEPES buffer solution (containing 0.1% BSA and 1% NaCl, pH 7.0) so as to obtain a concentration in first reagent of 2 µg/ml to 8 µg/ml, to make a first reagent.

2) Preparation of Second Reagent (Latex Particles Sensitized by Monoclonal Anti-HABP Antibody)

The same second reagent as prepared in Example 2 (1)2) was used.

3) Preparation of Hyaluronic Acid Solution

Sodium hyaluronate (produced by Kibun Food Chemifa Co., Ltd.) was diluted with 50 mM phosphate buffer solution (pH 7.0) so as to obtain a concentration in hyaluronic acid solution of 1,000 ng/mL, to make a hyaluronic acid solution.

(2) Measurement of Hyaluronic Acid

Using the hyaluronic acid solutions prepared in the above $(1)_3$ as a sample, absorbance at 805 nm of each sample was measured with a full automatic measurement system (JEOL Ltd., Model BM-8) under the following measurement conditions.

Sample: 2.4 μL

First reagent: 90 μL

Second reagent: 30

Measurement method: 2 point-end method

Main wavelength: 805 nm

Results obtained are shown in FIG. 6 (-◇-).

Value on the longitudinal axis in FIG. 6 is a value obtained by subtracting blank value (an absorbance when concentration of hyaluronic acid was 0) from an absorbance obtained by the measurement, and multiplying by 10,000.

Comparative Example 3

(1) Preparation of HABP Having the Known Amino Acid Sequence

The procedures of (1) Recovery of RNA to (5) Homology search of the nucleotide sequence in Example 1 were performed, and for the obtained cDNA, amendment of the nucleotide sequence was carried out using Mutan-K (produced by Takara Bio, Inc.) according to the product protocol.

Namely, as described above, in the known amino acid sequence of Bos Taurus aggrecan, the nucleotide sequence encoding amino acids in positions 129 to 130 from N-terminal (Ile-Leu) were "ATTCTA", while the nucleotide sequence in positions 388 to 393 of cDNA obtained in Example 1(5) corresponding to the above-described part of the known Bos Taurus aggrecan were "ATCTAT". Therefore, using the cDNA obtained in Example 1(5), a processing to change the nucleotide sequence in positions 388 to 393 of the cDNA from "ATCTAT" to "ATTCTA" was carried out.

After that, mapping of the nucleotide sequence of the amended cDNA prepared by the above-described processing was carried out using Base Station (produced by Biorad Laboratories, Inc.). And, it was confirmed that the nucleotide sequence of the amended cDNA was identical to the known nucleotide sequence encoding the amino acid sequence from N-terminal to the amino acid residue in position 692 of the known Bos Taurus aggrecan (SEQ ID NO: 8) (i.e. encoding the amino acid sequence in which amino acid residues in positions 129 and 130 from N-terminal were Ile-Leu of the known Bos Taurus aggrecan.).

After that, a recombinant vector pVL1392/amended cDNA was prepared by the same method as in Example 1(4), except that using the amended cDNA obtained as described above was used instead of the PCR product fragment prepared in Example 1(3) as a recombinant vector.

By expressing the amended cDNA by the same method as in the Example 1(6) to (7) except that the obtained recombinant vector pVL1392/amended cDNA was used, HABP having the same amino acid sequence as the known amino acid sequence from N-terminal to the position 693 of Bos Taurus aggrecan disclosed in the database (the sequence shown in SEQ ID NO: 9) (hereinafter, described as "HABP of the known amino acid sequence") was obtained.

(2) Preparation of Reagent

1) Preparation of First Reagent (Containing the HABP of the Known Amino Acid Sequence)

The HABP of the known amino acid sequence obtained in the above (1) was dissolved in 100 mM HEPES buffer solution (containing 0.1% BSA and 1% NaCl, pH 7.0) so as to obtain a concentration in a first reagent of 2 μg/ml to 8 μg/ml, to make a first reagent.

2) Preparation of Second Reagent (Latex Particles Sensitized by Monoclonal Anti-HABP Antibody)

The same second reagent as prepared in Example 4(1)2) was used.

3) Hyaluronic Acid Solution

The same hyaluronic acid solution as prepared in Example 4(1)3) was used.

(2) Measurement of Hyaluronic Acid

Using the hyaluronic acid solutions prepared in the above (1)3) as a sample, absorbance at 805 nm of each sample was measured with the same equipment and by the same method as in Example 4(2).

(3) Results

Results obtained are shown with solid quadrate (-■-) in FIG. 6 together with results of Example 4.

As is clear from the results of FIG. 6, when measurement of hyaluronic acid was carried out using "the HABP having known amino acid sequence obtained by expressing the cDNA prepared based on the nucleotide sequence of known Bos Taurus aggrecan disclosed in the database", rise of the absorbance was low even when concentration of the HABP of known amino acid sequence is increased, that is, sensitivity is low. Consequently, it can be understood that measurement cannot be performed when hyaluronic acid concentration in serum is low.

On the other hand, when measurement of hyaluronic acid was carried out using the HABP of the present invention, the absorbance was increased in accordance with the increase of the concentration of the HABP of the present invention. That is, it can be found that a sensitivity sufficient for the measurement of hyaluronic acid can be obtained by preparing the concentration of the HABP.

In addition, as is clear from the above-described facts, since the HABP of the present invention has a sufficient reactivity to perform hyaluronic acid measurement, it can be found that the present invention has an effect that a measurement kit for measuring hyaluronic acid in a certain concentration range may be provided by using a certain concentration of the HABP, when the HABP of the present invention is used.

INDUSTRIAL APPLICABILITY

Since the HABP of the present invention is a recombinant product, the HABP can be obtained at an inexpensive cost and in a large amount, and has superior quality with no fluctuation in quality, in comparison with native aggrecan.

In addition, since the HAPB of the present invention has features described above, inexpensive and high-accuracy measurement of hyaluronic acid can be performed using this.

EXPLANATION OF SYMBOLS

In FIG. 4, (-○-) shows the results when measurements were carried out using the first reagent containing the HABP of the present invention, and (-◆-) shows the results when measurements were carried out using the first reagent containing the native HABP.

In FIG. 5, (-○-) shows the results when measurements were carried out using the first reagent containing the HABP of the present invention, and (-◆-) shows the results when measurements were carried out using the first reagent containing the native HABP.

In FIG. 6, (-○-) shows the results when measurements were carried out using the first reagent containing the HABP of the present invention, and (-■-) shows the results when measurements were carried out using the first reagent containing the HABP having the known amino acid sequence.

The invention claimed is:

1. An isolated protein having a hyaluronic acid binding ability, wherein the protein comprises an amino acid sequence shown in SEQ ID NO: 2; an amino acid residue in position 130 from N-terminal of the amino acid sequence is isoleucine; and an amino acid residue in position 131 is an amino acid residue selected from the group consisting of tyrosine residue, serine residue, threonine residue, cysteine residue, asparagine residue and glutamine residue.

2. The isolated protein having a hyaluronic acid binding ability according to claim 1, wherein the amino acid sequence is SEQ ID NO: 4.

3. A method for measuring hyaluronic acid, comprising;
   contacting a hyaluronic acid in a sample with the protein having a hyaluronic acid binding ability according to claim 1 to form a complex of the hyaluronic acid and the protein,
   reacting the complex with a carrier supporting an antibody specific to the protein, measuring an optical change by an agglutinate obtained from the reaction, and
   calculating an amount of the hyaluronic acid from the measured value.

4. The method according to claim 3, wherein the carrier is latex.

5. A reagent kit for measuring hyaluronic acid, comprising the isolated protein having a hyaluronic acid binding ability according to claim 1 as a constituent.

* * * * *